(12) United States Patent
Polakiewicz et al.

(10) Patent No.: US 7,731,964 B2
(45) Date of Patent: Jun. 8, 2010

(54) ANTIBODIES SPECIFIC FOR PHOSPHORYLATED INSULIN RECEPTOR SUBSTRATE-1/2 (SER1101/SER1149) AND USES THEREOF

(75) Inventors: Roberto Polakiewicz, Lexington, MA (US); Jiong Wu, Reading, MA (US); Yu Li, Andover, MA (US)

(73) Assignee: Cell Signaling Technology, Inc., Danvers, MA (US)

( * ) Notice: Subject to any disclaimer, the term of this patent is extended or adjusted under 35 U.S.C. 154(b) by 1529 days.

(21) Appl. No.: 10/694,874

(22) Filed: Oct. 28, 2003

(65) Prior Publication Data

US 2004/0097713 A1 May 20, 2004

Related U.S. Application Data

(60) Provisional application No. 60/422,409, filed on Oct. 30, 2002.

(51) Int. Cl.
*A61K 39/00* (2006.01)
*A61K 39/395* (2006.01)
*C07K 16/00* (2006.01)

(52) U.S. Cl. ............... 424/139.1; 424/141.1; 530/387.9
(58) Field of Classification Search ........................ None
See application file for complete search history.

(56) References Cited

U.S. PATENT DOCUMENTS 4,208,479 A * 6/1980 Zuk et al. ..................... 435/7.9
5,593,678 A * 1/1997 Evans et al. ............... 424/184.1
5,621,075 A 4/1997 Kahn et al.
5,807,702 A * 9/1998 Mukerji et al. ............. 435/69.1

OTHER PUBLICATIONS

Sigma Chemical Co. 1998; p. 1308.*
Saltiel et al., *Nature* 414: 799-806 (2001).
White, M.F., *Mol. Cell. Biochem*. 182: 3-11 (1998).
Holgado-Madruga et al., *Nature* 379: 560-564 (1996).
Moodie et al., *J. Biol. Chem.*. 274: 11186-11193 (1999).
Saltiel et al., *Trends Cell Bio*. 12: 65-71 (2002).
Zick Y., *Trends Cell bio*. 11: 437-441 (2001).
Jiang et al., *Diabetes* 48: 1120-1130 (1999).
Mothe et al., *J. Biol. Chem*. 271: 9351-9356 (1996).
Li J., *J. Biol. Chem*. 274: 9351-9356 (1999).
Aguirre et al. J. Biol. Chem. 275: 9047-9054 (2000).
Rui et al., *J. Clin. Invest*. 107: 181-189 (2001).
Aguirre et al., *J. Biol. Chem*. 277: 1531-1537 (2002).
Griffin et al., *Diabetes* 48: 1270-1274 (1999).
Itani et al., *Metabolism* 50: 553-557 (2001).
Qu et al., *J. Endocrinol*. 162: 207-214 (1999).
Chalfant et al., *Endocrinology* 141: 2773-2778 (2000).
Solow, et al., *Molecular Endocrinology*, vol. 13 No. 10, pp. 1784-1798 (1999).

* cited by examiner

*Primary Examiner*—G. R Ewoldt
(74) *Attorney, Agent, or Firm*—CST Legal Dept.

(57) ABSTRACT

The invention discloses newly-discovered phosphorylation sites in human IRS-1 and IRS-2, serine 1101 (Ser1101) and serine 1149 (Ser1149) respectively, and provides antibodies, both polyclonal and monoclonal, that selectively bind to IRS-1 and/or IRS-2 when phosphorylated at these respective sites, but do not bind to IRS-1 and/or IRS-2 when not phosphorylated at these respective sites. The sites are relevant to insulin-resistance in type 2 diabetes. Also provided are methods for determining the phosphorylation of IRS-1/2 or activity of PKC theta in a biological sample, by using a detectable reagent, such as the disclosed antibodies, that binds to IRS-1/2 only when phosphorylated at Ser1101/Ser1149. Kits comprising the phosphor-IRS-1/2 (Ser1101/1149) antibodies of the invention are also provided.

22 Claims, 14 Drawing Sheets

Figure 1: Human IRS-1 protein sequence (SEQ ID NO: 1)

```
   1 masppesdgf sdvrkvgylr kpksmhkrff vlraaseagg parleyyene kkwrhkssap
  61 krsiplescf ninkradskn khlvalytrd ehfaiaadse aeqdswyqal lqlhnrakgh
 121 hdgaaalgag ggggscsgss glgeagedls ygdvppgpaf kevwqvilkp kglgqtknli
 181 giyrlcltsk tisfvklnse aaavvlqlmn irrcghsenf ffievgrsav tgpgefwmqv
 241 ddsvvaqnmh etileamram sdefrprsks qsssncsnpi svplrrhhln npppsqvglt
 301 rrsrtesita tspasmvggk pgsfrvrass dgegtmsrpa svdgspvsps tnrthahrhr
 361 gsarlhppln hsrsipmpas rcspsatspv slsssstsgh gstsdclfpr rssasvsgsp
 421 sdggfissde ygsspcdfrs sfrsvtpdsl ghtppargee elsnyicmgg kgpstltapn
 481 ghyilsrggn ghrctpgtgl gtspalagde aasaadldnr frkrthsagt sptithqktp
 541 sqssvasiee ytemmpaypp gggsggrlpg hrhsafvptr sypeeglemh plerrgghhr
 601 pdsstlhtdd gympmspgva pvpsgrkgsg dympmspksv sapqqiinpi rrhpqrvdpn
 661 gymmmspsgg cspdigggps sssssnavp sgtsygklwt ngvgghhshv lphpkppves
 721 sggkllpctg dymnmspvgd sntsspsdcy ygpedpqhkp vlsyyslprs fkhtqrpgep
 781 eegarhqhlr lstssgrlly aataddssss tssdslgggy cgarlepslp hphhqvlqph
 841 lprkvdtaaq tnsrlarptr lslgdpkast lprareqqqq qqpllhppep kspgeyvnie
 901 fgsdqsgyls gpvafhssps vrcpsqlqpa preeetgtee ymkmdlgpgr raawqestgv
 961 emgrlgpapp gaasicrptr avpssrgdym tmqmscprqs yvdtspaapv syadmrtgia
1021 aeevslprat maaassssaa sasptgpqga aelaahssll ggpqgpggms aftrvnlspn
1081 rnqsakvira dpqgcrrrhs setfsstpsa trvgntvpfg agaavggggg sssssedvkr
1141 hssasfenvw lrpgelggap kepaklcgaa gglenglnyi dldlvkdfkq cpqectpepq
1201 ppppppphqp lgsgessstr rssedlsaya sisfqkqped rq
```

Figure 2: Human IRS-2 protein sequence (SEQ ID NO: 2)

```
   1 maspprhgpp gpasgdgpnl nnnnnnnnhs vrkcgylrkq khghkrffvl rgpgaggdka
  61 tagggsapqp prleyyesek nwrskagapk rvialdccln inkradpkhk ylialytkde
 121 yfavaaeneq eqegwyralt dlvsegraaa gdappaaapa ascsaslpga vggsagaaga
 181 edsyglvapa taayrevwqv nlkpkglgqs knltgvyrlc lsartigfvk lnceqpsvtl
 241 qlmnirrcgh sdsfffievg rsavtgpgel wmqaddsvva qnihetilea mkalkelfef
 301 rprsksqssg ssathpisvp garrhhhlvn lppsqtglvr rsrtdslaat ppaakcsscr
 361 vrtasegdgg aaagaaaaga rpvsvagspl spgpvrapls rshtliggcr aagtkwhcfp
 421 aggglqhsrs msmpvehlpp aatspgslss ssdhgwgsyp pppgphpllp hplhhgpgqr
 481 pssgsasasg spsdpgfmsl deygsspgdl rafcshrsnt pesiaetppa rdgggggefy
 541 gymtmdrpls hcgrsyrrvs gdaaqdldrg lrkrtysltt parqrpvpqp ssasldeytl
 601 mratfsgsag rlcpscpass pkvayhpype dygdieigsh rssssnlgad dgympmtpga
 661 alagsgsgsc rsddympmsp asvsapkqil qpraaaaaaa avpfagpagp aptfaagrtf
 721 pasgggykas spaesspeds gymrmwcgsk lsmehadgkl lpngdylnvs psdavttgtp
 781 pdffsaalhp ggeplrgvpg ccysslprsy kapytcggds dqyvlmsspv grileeerle
 841 pqatpgptqa asafgagptq pphpvvpspv rpsggrpegf lgqrgravrp trlsleglps
 901 lpsmheyplp pepkspgeyi nidfgepgar lsppapplla saasssslls asspalslgs
 961 gtpgtssdsr qrsplsdymn ldfsspkspk pgapsghpvg sldgllspea sspypplppr
1021 psaspssslq pppppppapge lyrlppasav ataqgpgaas slssdtgdng dytemafgva
1081 atppqpiaap pkpeaarvas ptsgvkrlsl meqvsgveaf lqasqppdph rgakviradp
1141 qggrrrhsse tfsstttvtp vspsfahnpk rhnsasvenv slrksseggv gvgpggggdep
1201 ptsprqlqpa pplapqgrpw tpgqpgglvg cpgsggspmr retsagfqng lkyialdvre
1261 epglppqpqp pppplpqpgd ksswgrtrsl gglisavgvg strggcggpg pgapapcptt
1321 yaqh
```

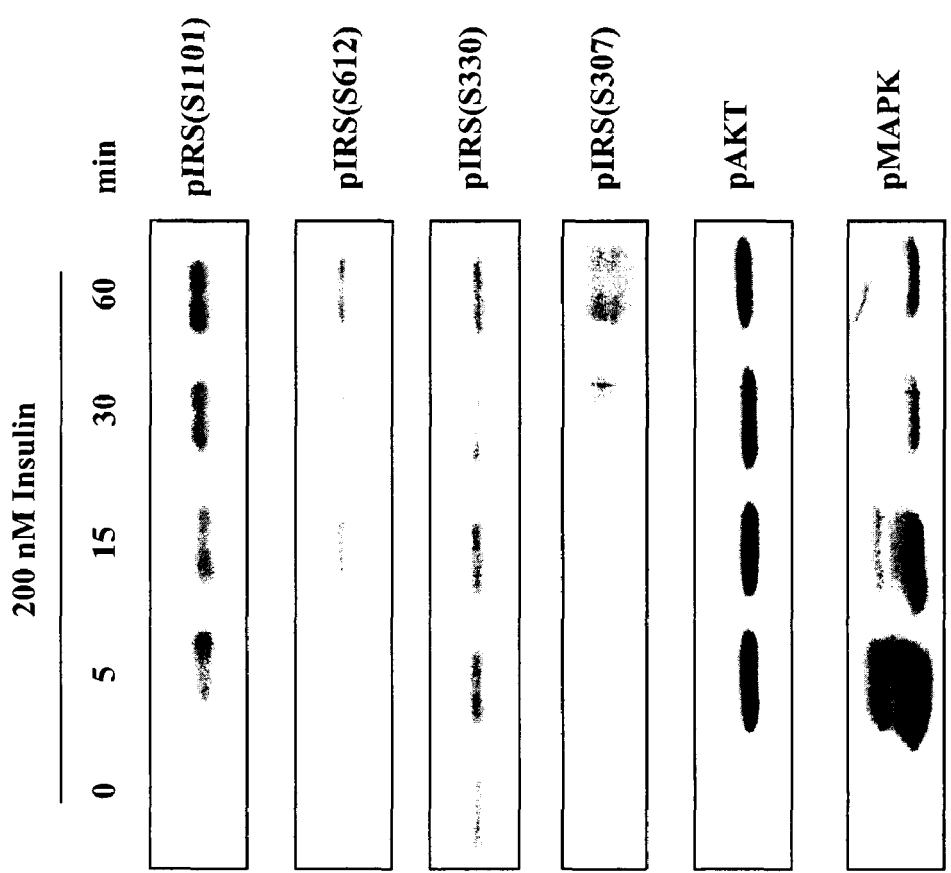
Figure 3: Serine phosphorylation of IRS-1 in CHO/IR/IRS-1 cells

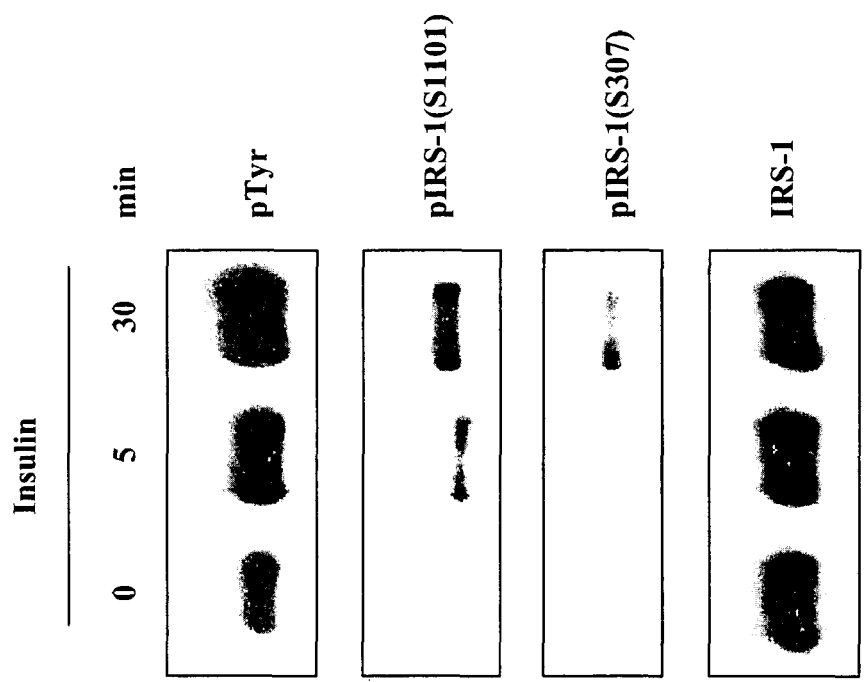
Figure 4: Phosphorylation of IRS-1 in 3T3L1 fat cells

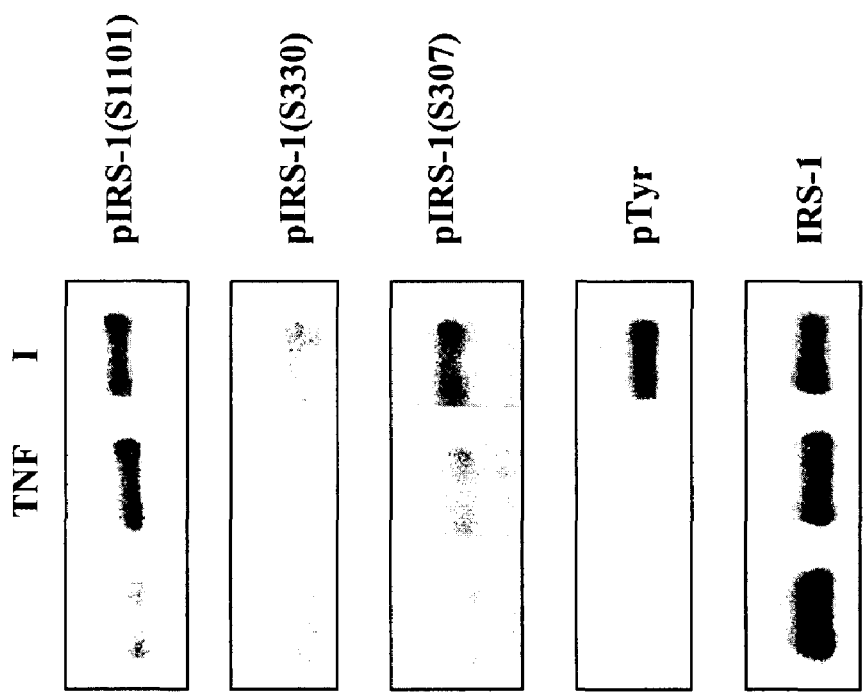
Figure 5: Phosphorylation of IRS-1 in L6 myocytes

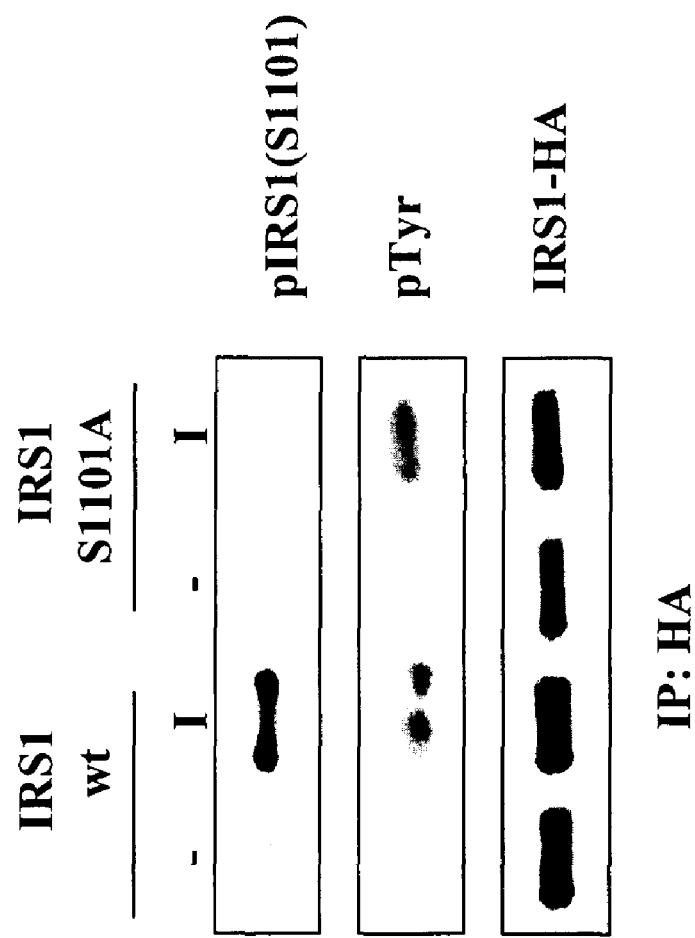
Figure 6: Specificity of pIRS-1(Ser1101) antibody

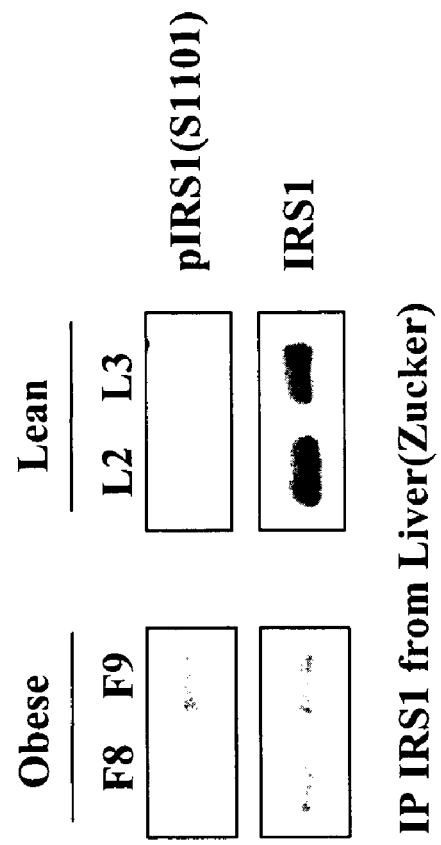
Figure 7: Phosphorylation of IRS-1 at Ser1101 in liver of Zucker rats

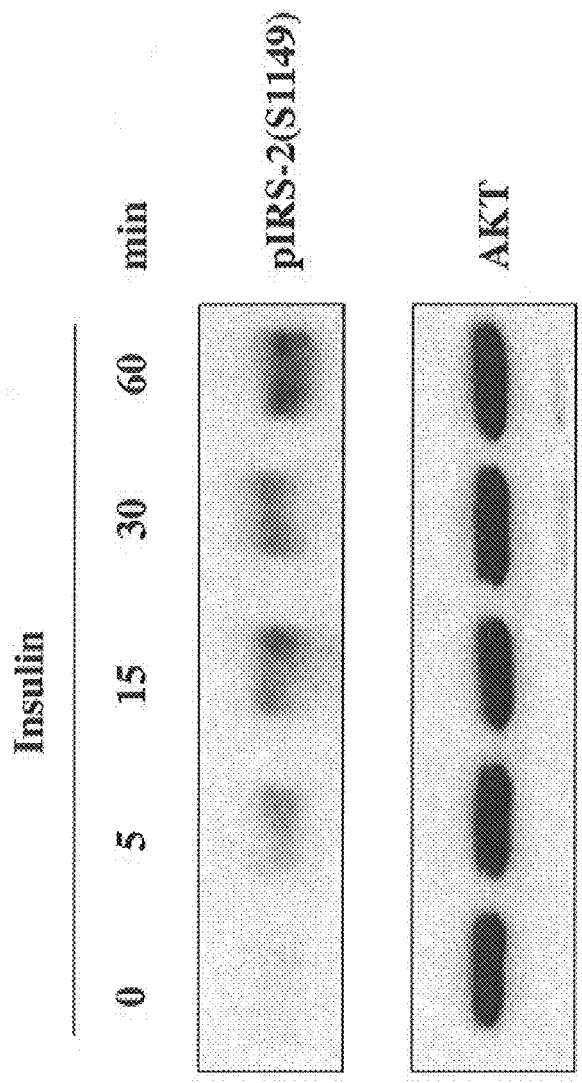
Figure 8: Phosphorylation of IRS-2 at Ser1149 in CHO cells
IRS-1 S1101: GCRRRHS*SETFSSTP (SEQ ID NO.: 7)
IRS-2 S1149: GGRRRHS*SETFSSTT (SEQ ID NO.: 8)

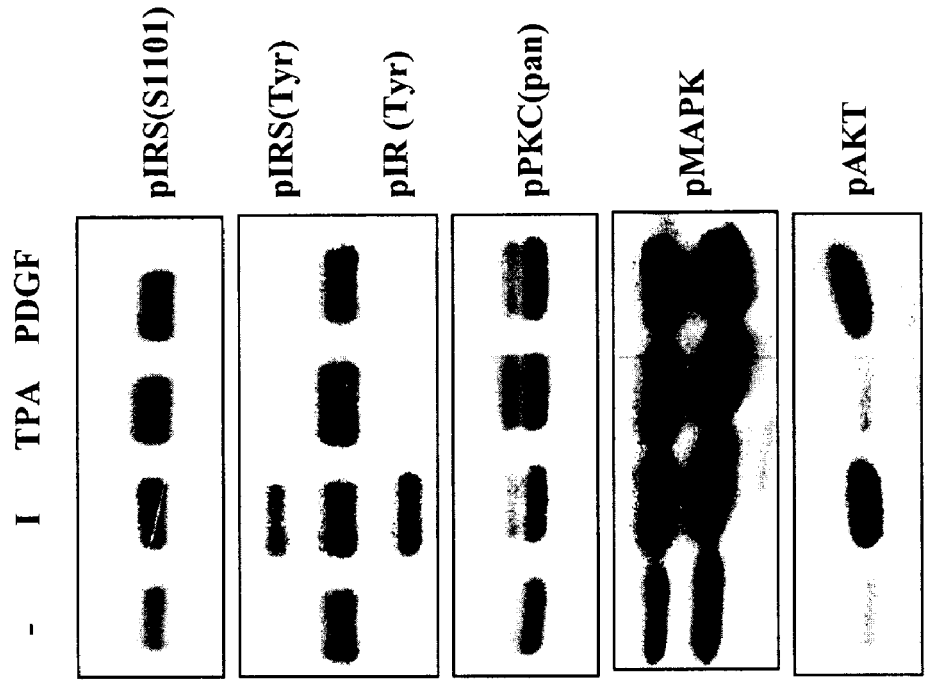
Figure 9: Phosphorylation of IRS1 at Ser1101 correlates with PKC activation

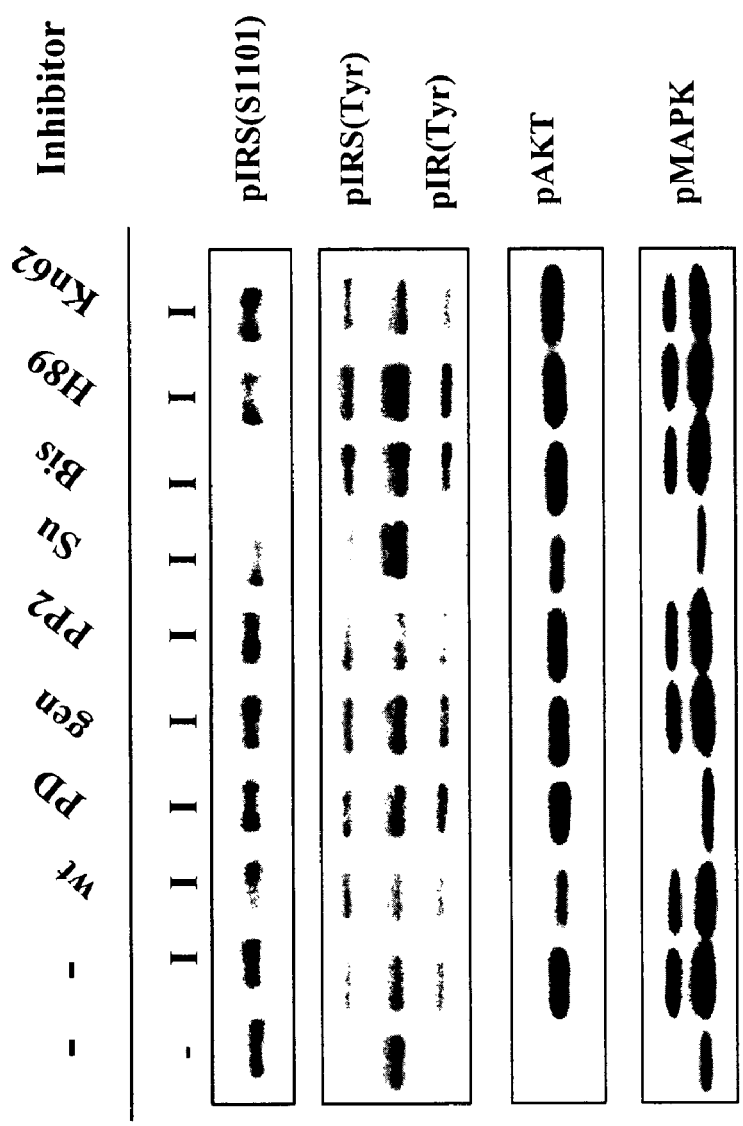
Figure 10: Phosphorylation of IRS1 at Ser1101 is blocked by PKC inhibition

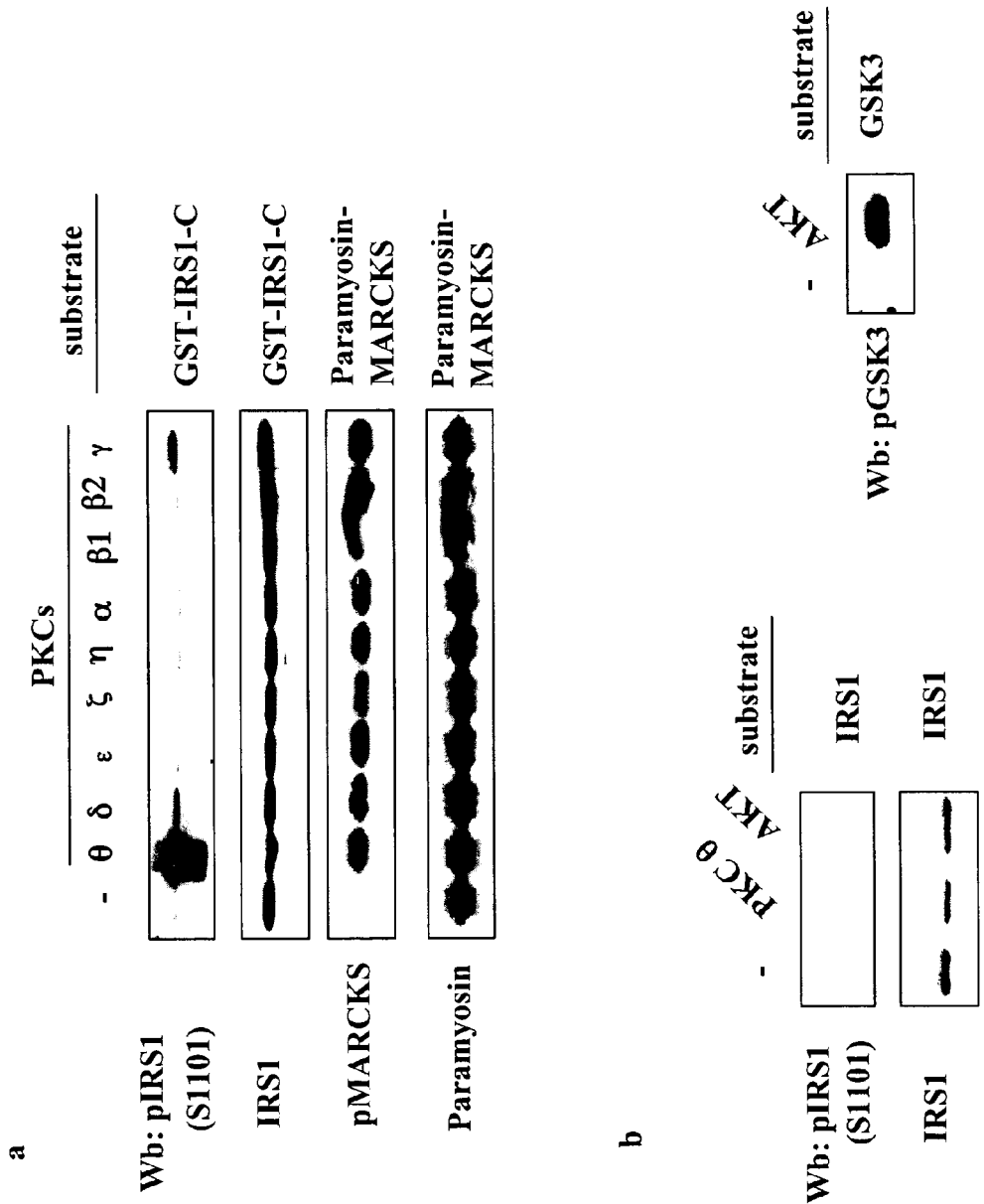
Figure 11: PKCθ kinase phosphorylates IRS-1(Ser1101) in vitro

Figure 12: PKCθ kinase phosphorylates IRS-1(Ser1101) in vivo
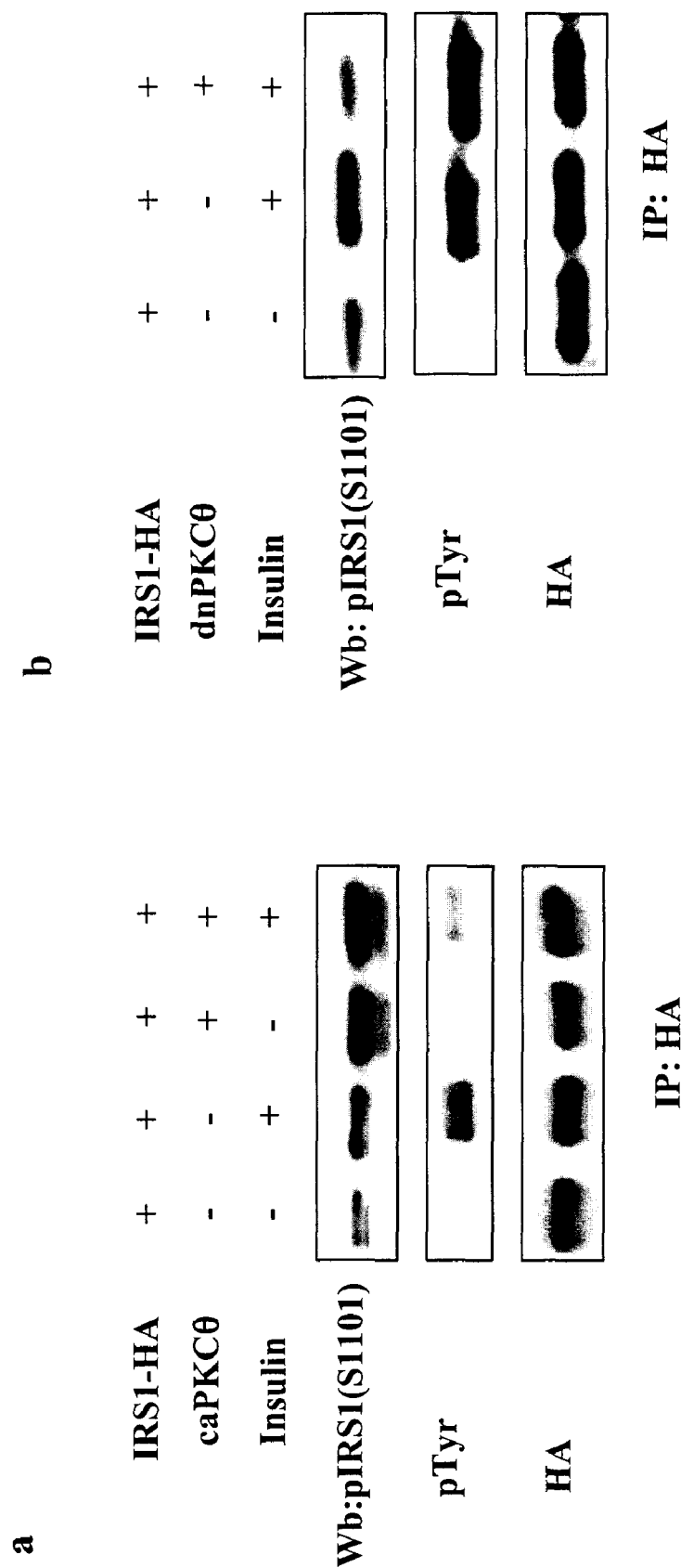

Figure 13: Mouse IRS-1 protein sequence (SEQ ID NO: 3)

```
   1 masppdtdgf sdvrkvgylr kpksmhkrff vlraaseagg parleyyene kkwrhkssap
  61 krsiplescf ninkradskn khlvalytrd ehfaiaadse aeqdswyqal lqlhnrakah
 121 hdgagggcgg scsgssgvge agedlsydtg pgpafkevwq vilkpkglgq tknligiyrl
 181 cltsktisfv klnseaaavv lqlmnirrcg hsenfffiev grsavtgpge fwmqvddsvv
 241 aqnmhetile amramsdefr prsksqssss csnpisvplr rhhlnnppps qvgltrrsrt
 301 esitatspas mvggkpgsfr vrassdgegt msrpasvdgs pvspstnrth ahrhrgssrl
 361 hpplnhsrsi pmpssrcsps atspvslsss stsghgstsd clfprrssas vsgspsdggf
 421 issdeygssp cdfrssfrsv tpdslghtpp argeeelsny icmggkgast laapnghyil
 481 srggnghryi pganlgtspa lpgdeaagaa dldnrfrkrt hsagtsptis hqktpsqssv
 541 asieeytemm paayppgggs ggrlpgyrhs afvpthsype eglemhhler rgghhrpdts
 601 nlhtddgymp mspgvapvps nrkgngdymp mspksvsapq qiinpirrhp qrvdpngymm
 661 mspsgscspd igggsssssss isaapsgssy gkpwtngvgg hhthalphak ppvesgggkl
 721 lpctgdymnm spvgdsntss psecyygped pqhkpvlsyy slprsfkhtq rpgepeegar
 781 hqhlrlssss grlrytatae dsssstssds lgggycgarp esslthphhh vlqphlprkv
 841 dtaaqtnsrl arptrlslgd pkastlprvr eqqqqqqssl hppepkspge yvniefgsgq
 901 pgylagpats rsspsvrcpp qlhpapreet gseeymnmdl gpgrratwqe sggvelgrig
 961 pappgsatvc rptrsvpnsr gdymtmqigc prqsyvdtsp vapvsyadmr tgiaaekasl
1021 prptgaappp sstasssvtp qgataeqath ssllggpqgp ggmsaftrvn lspnhnqsak
1081 viradtqgcr rrhssetfsa ptragntvpf gagaavggsg gggggsedv krhssasfen
1141 vwlrpgdlgg vskesapvcg aaggleksln yidldlaker sqdcpsqqqs lpppphqpl
1201 gsnegnsprr ssedlsnyas isfqkqpedr q
```

Figure 14: Mouse IRS-2 protein sequence (SEQ ID NO: 4)

1 masaplpgpp asggggdgpnl nnnnnnnnhs vrkcgylrkq khghkrffvl rpgtggdea
61 saaggsppqp prleyyesek kwrskagapk rvialdccln inkradakhk ylialytkde
121 yfavaaeneq eqegwyralt dlvsegrsge ggsgttggsc saslpgvlgg sagaagcddn
181 yglvtpatav yrevwqvnlk pkglgqsknl tgvyrlclsa rtigfvklnc egpsvtlqln
241 nirrcghsds fffievgrsa vtgpgelwmq addsvvaqni hetileamka lkelfefrpr
301 sksqssgssa thpisvpgar rhhhlvnlpp sqtglvrrsr tdslaatppa akctscrvrt
361 asegdggaag gagtaggrpm svagsplspg pvraplsrsh tlsagcggrp skvtlapagg
421 alqhsrsnsm pvahsppaat spgslssssg hgsgsyplpp gshphlphpl hhpqgqrpss
481 gsasasgsps dpgfmsldey gsspgdlraf sshrsntpes iaetppardg sggelygyms
541 mdrplshcgr pyrrvsgdga qdldrglrkr tyslttparq rqvpqpssas ldeytlmrat
601 fsgssgrlcp sfpasspkva ynpypedygd ieigshksss snlgaddgym pmtpgaalrs
661 ggpnscksdd ympmsptsvs apkqilqprl aaalppsgaa vpappsgvgr tfpvngggyk
721 asspaesspe dsgymrmwcg sklsmenpdp kllpngdyln kspseagtag tppdfsaalr
781 ggseglkgip ghcyssslprs ykapcscsgd ndqyvlmssp vgrileeerl epqatpgagt
841 fgaaggshtq phhsavpssm rpsaiggrpe gflgqrcrav rptrlslegl qtlpsmqeyp
901 lptepkspge yinidpgeag trlsppappl lasaassssl lsasspassl gsgtpgtssd
961 srqrsplsdy mnldpsspks pkpstrsgdt vgsmdgllsp easspypplp prpstspssl
1021 qqplppapgd lyrlppasaa tsqgptagss mssepgdngd ysemafgvaa tppqpivapp
1081 kpegarvasp tsglkrlslm dqvsgveafl qvsqppdphr gakviradpq ggrrrhsset
1141 fssttttvtpv spsfahnskr hnsasvenvs lrkssegsst lgggdeppts pgqaqplvav
1201 ppvpqarpwn pgqpgaligc pggssspmrr etsvgfqngl nyiaidvrge qgslaqsqpq
1261 pgdknswsrt rslgglligtv ggsgasgvcg gpgtgalpsa styasidfls hhlkeatvvk
1321 e ANTIBODIES SPECIFIC FOR PHOSPHORYLATED INSULIN RECEPTOR SUBSTRATE-1/2 (SER1101/SER1149) AND USES THEREOF

RELATED APPLICATIONS

This application claims priority to U.S. Ser. No. 60/422,409, filed Oct. 30, 2002, the disclosure of which is hereby incorporated herein.

FIELD OF THE INVENTION

The invention relates generally to antibodies, and more particularly to antibodies to signal transduction proteins and their uses.

BACKGROUND OF THE INVENTION

One of the major physiological roles of insulin is to stimulate glucose transport into insulin-sensitive cells and tissues by inducing the translocation of the major insulin responsive glucose transporter, GLUT4, from an intracellular compartment to the plasma membrane. Secretion of insulin from the beta cells in the pancreas thus tightly regulates glucose homeostasis, which is critical for normal physiologic maintenance in higher animals.

Insulin resistance, which is commonly associated with prevalent type 2 diabetes, is a state in which target cells fail to respond to normal levels of circulating insulin. See, e.g. Saltiel et al., *Nature* 414: 799-806 (2001). This lack of response, in turn, results in hyperinsulinemia to compensate for the resistance to insulin in the prediabetic state. Subsequently, hyperglycemia develops due to the failure of the pancreatic beta cells to produce and secrete enough insulin to compensate for the imbalance in glucose metabolism. Type 2 diabetes is the most common form of the disease, affecting 16 million people in the United States alone. (Source: American Diabetes Association). Roughly one-third of these people remain undiagnosed. (Source: id.)

At the molecular level, insulin resistance may result from mutations or posttranslational modifications of the insulin receptor or any of its downstream targets. The identification of simple molecular explanations for insulin resistance and type 2 diabetes has so far proven difficult. Understanding the basic mechanisms of insulin resistance at the molecular level could have a great impact on finding a cure for a chronic disease like type-2 diabetes and insulin resistance that develops in other conditions such as chronic obesity and acute trauma.

The insulin receptor (IR) is a transmembrane glycoprotein, comprising an extracellular insulin-binding domain and a transmembrane tyrosine protein kinase domain that undergoes autophosphorylation following insulin binding. Autophosphorylation in turn activates the IR intrinsic tyrosine kinase activity and triggers phosphorylation of numerous downstream targets that ultimately mediate insulin's several biological effects.

The major targets of insulin receptor kinase are the insulin-receptor substrate (IRS) proteins IRS-1, IRS-2, IRS-3, IRS-4, the adaptor proteins Shc, Gab1, APS, p60Dok, SIRPS and c-Cbl. See, e.g. White, M. F., *Mol. Cell. Biochem.* 182: 3-11 (1998); Kahn et al., U.S. Pat. No. 5,621,075, Issued Apr. 15, 1997; Holgado-Madruga, et al., *Nature* 379: 560-564 (1996); Sasaoka et al., *J. Biol. Chem.* 269: 13689-694 (1994); Moodie et al., *J. Biol. Chem.* 274:11186-193 (1999). The C-terminal region of IRS proteins contains multiple tyrosine phosphorylation motifs that serve as docking sites for many SH2 domain-containing proteins, such as the p85 regulatory subunit of PI3K, which mediate many of the down-stream biological actions of insulin. See, e.g. White (1998), supra.

The relative roles of the different IRS proteins in insulin signaling and diabetes have been intensively studied. Gene targeting experiments have revealed that IRS proteins are essential for normal development and metabolism. See, e.g. Saltiel et al., *Trends Cell Biol.* 12: 65-71 (2002). For example, mice lacking IRS-1 grow poorly in utero and remain small throughout life, but diabetes does not develop because insulin secretion increases to compensate for a mild insulin resistance. In contrast, IRS-2 null mice develop insulin resistance and beta cell failure, and die from type 2-like diabetes. These results not only suggest a critical role of IRS proteins in mediating insulin action, but also indicate that understanding the regulation of IRS proteins can provide important clues as to the causes of insulin resistance.

Protein phosphorylation is an important mechanism by which the activity of the insulin-signaling pathway, as with most signaling pathways, is regulated. A major negative regulatory mechanism for insulin action has been attributed to agents that enhance serine or threonine (Ser/Thr) phosphorylation of either the IR itself, or of its downstream effectors. Ser/Thr phosphorylation reduces the tyrosine kinase activity of the IR, and thus its ability to phosphorylate substrate proteins. For example, insulin's counter regulators, such as epinephrine and glucagons, increase cAMP levels in the cell, thereby activating the cAMP-dependent protein kinase (PKA) and increasing the Ser/Thr phosphorylation of the insulin receptor, which results in an insulin-resistant state. Similarly, the general inhibitor of protein phosphatases, okadaic acid, inhibits tyrosine phosphorylation of IRS-1, while increasing its phosphorylated Ser/Thr content. Tumor necrosis factor-α, a known mediator of insulin resistance during infection, tumor cachexia, and obesity all cause similar effects.

It has been postulated that phosphorylation of serine residues significantly reduces the ability of IRS-1 and IRS-2 to interact with, and become, tyrosine phosphorylated by the IR. See, e.g. White (1998), supra.; Zick Y., *Trends Cell Biol.* 11: 437-441 (2001); Saltiel et al. (2002), supra. Phosphorylation of IRS at Ser/Thr residues and the consequent inactivation of insulin signaling can be triggered by prolonged exposure to insulin itself or by cross-desensitization with other factors that provoke IRS phosphorylation, e.g. PDGF, IGF-1 endothelin, or TNFα.

However, there is mounting evidence indicating that each stimulus can desensitize IRS-1 and IRS-2 function through a different mechanism, implying the phosphorylation of different sites in the IRS proteins. Indeed, IRS proteins contain over 30 potential Ser/Thr phosphorylation sites for kinases like PKA, PKC, mitogen-activated protein kinase (MAPK), Akt (PKB) and others. See, e.g. White (1998), supra.; Zick, supra.; Saltiel et al. (2002), supra. For example, stimulators of PKC, such as phorbol esters or endothelin, induce the activity of MAPK, which then phosphorylates IRS-1 at Ser612. See, e.g. Jiang et al., *Diabetes* 48: 1120-1130(1999); Mothe et al., *J. Biol. Chem.* 271:9351-9356(1996). This phosphorylation event reduces IRS-1 tyrosine phosphorylation by the IR, as well as IRS-1 association with PI3K. In contrast, the inhibitory effects of PDGF were reported to not require Ser612, but instead phosphorylation of three other serine residues (632, 662, and 731) were involved through a mechanism implicating PI3K/Akt and mTOR pathway. See Li J., *J. Biol. Chem.* 274: 9351-9356 (1999). Phospho-specific antibodies to certain of these IRS-1 phosphorylation sites are commercially available. (See, e.g. Upstate Biotechnology, Inc., Cat. No. 07-247(Ser307); Cell Signaling Technology, Inc., Cat. Nos. 2388, 2386 (Ser 636/639 and 612); BioSource, Inc., Cat. No. 44-550 (Ser616)).

The protein kinase Akt, however, has been implicated in positively modulating IRS function by preventing its rapid tyrosine phosphorylation. See Zick, supra. The action of Akt appears to involve four possible serine residues in human IRS (270, 307, 330, and 383), but the evidence on which of these sites is essential for negative or positive regulation by Akt is inconclusive. Other recent studies suggest that Ser312 (307 in the mouse) in IRS-1 is actually regulated by TNF-α through activation and direct phosphorylation by the Jun-terminal kinase (JNK), a kinase of the MAPK family. See, e.g. Aguirre et al., *J. Biol. Chem.* 275: 9047-9054 (2000); Rui et al., *J. Clin. Invest.* 107. 181-189 (2001); Aguirre et al., *J. Biol. Chem.* 277:1531-1537 (2002). This finding could explain the well-documented insulin resistance that is provoked by acute stress and mediated through TNF-α action.

Taken together, these results underscore the important role that IRS-1 Ser/Thr phosphorylation plays in type 2 diabetes. However, the precise mechanisms by which particular signaling events are mediated by IRS-1 phosphorylation remain unclear, and the serine or threonine residues relevant to such mechanisms remain unidentified. For example, chronic and acute elevation of plasma free fatty acid is commonly linked to impaired insulin-mediated glucose uptake. See Griffin et al., *Diabetes* 48:1270-1274 (1999). The mechanisms underlying these changes in glucose transport are unknown, but may include changes in insulin signaling. It has been shown that protein kinase C (PKC) theta protein levels, one of the major PKC isoforms expressed in skeletal muscle, are elevated in insulin resistant humans and rats. Moreover, PKC theta activity is enhanced by elevated plasma free-fatty acids. See Itani et al., *Metabolism* 50: 553-557 (2001); Qu et al., *J. Endocrinol.* 162: 207-214 (1999); Chalfant et al., *Endocrinology* 141: 2773-2778 (2000). PKC theta thus represents a potential therapeutic target for modulating insulin signaling in obesity-driven insulin resistance, but the mechanism of its action remains unclear.

Accordingly, there remains a need for the identification of Ser/Thr phosphorylation sites in IRS-1 and IRS-2 that are essential for the inhibition of insulin signaling leading to insulin resistance and type 2 diabetes. The production of phospho-specific antibodies directed at such sites would greatly facilitate the elucidation of critical phosphorylated Ser/Thr residues in IRS-1 and IRS-2, particularly in the context of the diverse pathological circumstances and pathways that cause insulin resistance. Such antibodies would be valuable tools for the early diagnosis of type-2 diabetes and other conditions involving insulin resistance, as well as for drug discovery programs aimed at identifying new compounds for the restoration of insulin-sensitivity in diabetic individuals.

SUMMARY OF THE INVENTION

The invention discloses a novel human IRS-1 phosphorylation site, serine 1101 (Ser1101), and a homologous novel phosphorylation site, serine 1149 (Ser1149) in human IRS-2, as well as homologous sites in mouse IRS-1 (Ser1095) and IRS-2 (Ser1138), and provides antibodies that selectively bind to IRS-1 and/or IRS-2 when phosphorylated at these novel sites. Also provided are methods for determining the phosphorylation of IRS-1 and/or IRS-2 in a biological sample, profiling IRS-1 and/or IRS-2 activation in a test tissue, and identifying a compound that modulates phosphorylation of IRS-1 and/or IRS-2, by using a detectable reagent, such as the disclosed antibodies, that binds to IRS-1 and/or IRS-2 when phosphorylated at Ser1101 and/or Ser1149, respectively. In preferred embodiments, the sample or test tissue is taken from a subject potentially having or suspected of having type 2 diabetes.

The invention further discloses that the novel human IRS-1 serine 1101 site identified herein (corresponding to ser1149 in IRS-2) is phosphorylated by protein kinase C theta (PKC theta (θ)). Accordingly, the invention also provides methods for determining the activity of PKC theta in a biological sample, profiling PKC theta activation in a test tissue, and identifying a compound that modulates PKC theta activity, by using a detectable reagent, such as the disclosed antibodies, that binds to IRS-1 when phosphorylated at Ser1101 and/or to IRS-2 when phosphorylated at Ser1149. In preferred embodiments, the sample or test tissue is taken from a subject potentially having, or suspected of having, a disease characterized by, or associated with, altered PKC theta activity, such as type 2 diabetes.

BRIEF DESCRIPTION OF THE DRAWINGS

FIG. 1—is the amino acid sequence (1-letter code) of human IRS-1 (SEQ ID NO: 1) (SwissProt Acc# P35568). Ser1101 is underlined, and the peptide sequence encompassing Ser1101 and corresponding to the immunogen used to generate an exemplary IRS-1 (Ser1101)/IRS-2 (Ser1149) phosphospecific antibody is indicated in bold (see Example 1).

FIG. 2—is the amino acid sequence (1-letter code) of human IRS-2 (SEQ ID NO: 2) (SwissProt Acc# Q9Y4H2). Ser1149 is underlined, and the peptide sequence encompassing Ser1149 and indicated in bold corresponds to the nearly-identical sequence in human IRS-1 (as shown in FIG. 1) that was used as an immunogen in Example 1.

FIGS. 3-5—are Western blot analyses using phospho-IRS-1 (Ser1101, Ser1330, or Ser1307) polyclonal antibodies and CHO cells overexpressing the IR and IRS-1 (FIGS. 2, 5 and 6), 3T3L1 adipocytes (FIG. 3) and differentiated L6 myocytes (FIG. 4). Cells were stimulated with insulin (200 nM), and TNFα (100 nM), as indicated, for 5 minutes (FIGS. 4,5), or for the times indicated (FIGS. 2-3). Cell extracts were prepared and subjected directly to SDS-PAGE and immunoblotting with the antibodies as indicated (FIGS. 2, 3, 6), or alternatively, IRS-1 was immunoprecipitated with an IRS-1 specific antibody and immunoblotted (FIGS. 3-5). Extracts from the same treated cells were immunoblotted with antibodies against phospho-Akt (Ser1473); phospho-MAPK (Thr202/Tyr204); phosphotyrosine (PY-100); and total IRS-1, which served as controls for verifying the stimulus and protein loading of the gels.

FIG. 6—is a Western blot analysis of IRS-1 protein carrying an HA epitope tagged after immunoprecipitation with an anti-HA antibody, and probed with the phospho-IRS-1/2 (Ser1101/Ser1149) antibody of the invention, a phosphotyrosine (pY-100) antibody), and anti-HA antibody, which served as controls for verifying the insulin stimulus (induction of IRS-1 tyrosine phoshorylation) and equivalent amounts of HA-tagged IRS-1 protein. Cells were previously transfected with HA-tagged IRS-1 wild type and IRS-1 carrying a mutation of Ser1101 to Alanine.

FIG. 7—is a Western blot analysis of IRS-1 protein immunoprecipitated with a total anti-IRS-1 antibody from liver extracts of lean and obese/diabetic Zucker rats and probed with the phospho-IRS-1 (Ser1101)/IRS-2 (Ser1149) antibody of the invention.

FIG. 8 shows a comparison of amino acid sequences around Ser 1101 and Ser 1149 in human IRS-1 and IRS-2, respectively (SEQ ID NO: 7 and SEQ ID NO: 8, respectively); below the sequences is a Western blot analysis of IRS-2 protein extracted from CHO cells overexpressing the IRS-2 protein. Phosphorylation of IRS-2 at Ser 1149 was induced by insulin treatment at different times as indicated. Total Akt protein immunoblots served as loading controls.

FIGS. 9 & 10—are Western blot analyses using phospho-IRS-1 (Ser1101)/IRS-2(Ser1149) polyclonal antibodies of the invention and CHO cells overexpressing the IR and IRS-1. Cells were stimulated with insulin (200 nM), TPA (200 nM), PDGF (100 nM) and TNFα (100 nM), as indicated, for 5 minutes. Cell extracts were prepared and subjected directly to SDS-PAGE and immunoblotting with the antibodies as indicated. Extracts from the same treated cells were immunoblotted with antibodies against phospho-Akt (Ser473); phospho-MAPK (Thr202/Tyr204); phosphotyrosine (PY-100); phospho-PKC(pan) and total IRS-1, which served as controls for verifying the stimulus and protein loading of the gels. In FIG. 10, cells were exposed to the following inhibitors prior to insulin stimulus: wortmannin (wt); PD98059 (PD); genistein (gen); PP2; SU6686 (SU); bis-indoleimide (bis); H89; KN62.

FIG. 11—is a Western Blot analysis indicating the in vitro phosphorylation of IRS-1 at Ser1101 by PKC theta. Active, purified PKC isoforms as indicated, including PKC theta and Akt kinases were used to phosphorylate, in vitro, a GST-IRS-1 C-terminus fusion protein containing Ser1101, full length IRS-1 immunoprecipitated from unstimulated CHO-IR/IRS-1 cell extracts, or a GSK3 fusion protein (known substrate for Akt) as a control of Akt activity. In panel b, PKC theta and Akt were used to phosphorylated in vitro, full length IRS-1 immunoprecipitated from CHO cell over expressing IRS-1 with an IRS-1 antibody.

FIG. 12—is a Western blot analysis describing the effects in vivo of a catalytically active PKC theta expression (panel a), or dominant negative PKC theta (panel b) on the phosphorylation of IRS-1 at Ser1101. NIH3T3 cells were co-transfected with expression constructs for these two PKC theta mutant proteins together with wild-type HA-tagged IRS-1, and stimulated with 200 nM insulin as indicated. IRS-1 proteins were immunoprecipitated with an anti-HA antibody and immunoblotted with phospho-IRS-1 (Ser1101)/IRS-2 (Ser1149) antibody of the invention, with a phosphotyrosine antibody (pY-100) to control for the efficacy of the insulin treatment, or with the anti-HA antibody to control for the amount of protein in the assay.

FIG. 13—is the amino acid sequence (1-letter code) of mouse IRS-1 (SEQ ID NO: 3) (SwissProt Acc# P35569). Ser1095 is underlined, and the peptide sequence encompassing Ser1095 and corresponding to the highly-homologous sequence of the human IRS-1 (Ser1101) phosphorylation site is indicated in bold (see FIG. 1).

FIG. 14—is the amino acid sequence (1-letter code) of mouse IRS-2 (SEQ ID NO: 4) (SwissProt Acc# P81122). Ser1138 is underlined, and the peptide sequence encompassing Ser1138 and indicated in bold corresponds to the highly-homologous sequence of the murine IRS-1 (Ser1095) and human IRS-2 (Ser1149) phosphorylation sites (see FIGS. 13 and 2).

DETAILED DESCRIPTION OF THE INVENTION

In accordance with the present invention, a novel site of IRS-1 phosphorylation, serine 1101 (Ser1101) in the human sequence (see FIG. 1), has now been identified. A highly homologous novel site of IRS-2 phosphorylation, serine 1149 (Ser1149) in the human sequence (see FIG. 2), has also now been identified, as well as novel, highly-homologous sites in mouse IRS-1 and IRS-2. Although IRS-1 phosphorylation at various serine residues has previously been described (Zick, supra. (serines 270, 307, 330, 383); Aguirre et al. (2000), supra. (serine 312); Li, supra. (serines 612, 632, 662, 731)), the serine phosphorylation site (Ser1101) disclosed herein has previously been unknown. Equivalent phosphorylation sites in IRS-2 have not been described.

The newly identified Ser 1101 phosphorylation site was identified/predicted by analyzing the human IRS-1 amino acid sequence with the ScanSite program (see Yaffe et al., *Nat Biotechnol.* 19(4): 348-53 (2001)). This algorithm searches for motifs within proteins that are likely to be phosphorylated by specific protein kinases or bind to domains such as SH2 domains, 14-3-3 domains or PDZ domains. Optimal phosphorylation sites for particular serine/threonine protein kinases or tyrosine protein kinases are predicted using a matrix of selectivity values for amino acids at each position relative to the phosphorylation site, as determined from the oriented peptide library technique described by Songyang et al., Current Biology 4: 973-982 (1994) and Songyang et al., Nature 373: 536-539 (1995).

Analysis of the human IRS-1 protein sequence with Scan-Site revealed several potential Ser/Thr phosphorylation sites, including putative Akt, Casein Kinase, GSK3 and PKCz sites. Attention was focused on the Akt sites due to the importance of the PI3K/Akt cascade in insulin/IRS signaling. The three sites identified, numbered according to human IRS-1 (FIG. 1, SEQ ID NO: 1), all include a typical Akt consensus (RRXRXXS) motif sequence, and are (phosphorylated serine indicated by bold *S):

Ser307: TRRSRTE*SITATSPA (SEQ ID NO: 5)
Ser330: SFRVRAS*SDGEGTMS (SEQ ID NO: 6)
Ser1101: GCRRRHS*SETFSSTP (SEQ ID NO: 7)

The potential role of Ser307 and Ser330 in IRS-1 phosphorylation has been reported. See Paz et al., *J. Biol. Chem.* 274: 28816-28822 (1999). However, the role of Ser1101 has not. Sequence comparison of the IRS-1 (Ser1101) phosphorylation site with human IRS-2 (SEQ ID NO: 2) identified a novel and highly homologous phosphorylation site at Ser1149 in IRS-2:

Ser1149: GGRRRHS*SETFSSTT (SEQ ID NO: 8).

Further sequence comparison of the human IRS-1 (Ser1101) and IRS-2 (Ser1149) sites, respectively, with the mouse IRS-1 and IRS-2 sequences identified novel and highly homologous phosphorylation sites at Ser1095 (IRS-1) and Ser1138 (IRS-2) in the mouse proteins as follows:

Ser1095: GCRRRHS*SETFSAPT (SEQ ID NO: 9);
Ser1138: GGRRRHS*SETFSSTT (SEQ ID NO: 10);

Phosphorylation of human IRS-1 at Ser1101 and IRS-2 at Ser1149 was confirmed using exemplary phospho-specific antibodies of the invention (see Examples). As a result of this discovery, peptide antigens may now be designed to raise phospho-specific antibodies that bind IRS-1 only when phosphorylated at Ser1101 and/or IRS-2 only when phosphorylated at Ser1149 in the human peptides sequences, and/or to the equivalent and highly-homologous sites in mouse IRS-1 and IRS-2 (Ser1095, Ser1138), or other species, such as rat (Ser1100 in IRS-1).

In further accordance with the present invention, is has now been shown that the novel IRS-1 (Ser1101) phosphorylation site is, in fact, phosphorylated by protein kinase C theta (PKC theta), the activity of which is increased in diabetic patients and insulin resistant animals (see Itani et al., supra.; Chalfant et al., supra.; Qu et al., supra.) Phosphorylation of IRS-1 at serine residues has been shown to correlate mostly with desensitization of the insulin stimulus, and, therefore, phosphorylation of IRS-1 at Ser1101 may represent an important surrogate marker of insulin resistance, which develops as a consequence of Type 2 diabetes. Given the high homology between the IRS-1 (Ser1101) and IRS-2 (Ser1149) phosphorylation sites (the latter is identical to the former except for two residues) it is expected that PKC theta will also phosphorylate IRS-2 (Ser1149). Thus, phosphorylation of IRS-2 (Ser1149) may also represent an important surrogate marker of insulin resistance in Type 2 diabetes.

Accordingly, the invention provides, in part, phospho-specific antibodies that bind to human IRS-1 and/or IRS-2 only when phosphorylated at serine 1101 and serine 1149, respectively, and do not recognize the unphosphorylated forms, or other IRS-1 or IRS-2 phosphorylation sites. Also provided are methods of using a detectable reagent that binds to phosphorylated IRS-1/2 (Ser1101/Ser1149) to detect IRS-1/2 phosphorylation and activation in a biological sample or test tissue potentially containing, or suspected of containing, phosphorylated IRS-1 and/or IRS-2, or having altered insulin signaling or IRS-1/2 activity, as further described below. The invention also provides, in part, methods of using a detectable reagent that binds to phosphorylated IRS-1/2 (Ser1101/Ser1149) to detect PKC theta activity in a biological sample, test tissue, or subject potentially having, or suspected of having, altered insulin signaling, PKC theta activity, or IRS-1 phosphorylation, as further described below. In preferred embodiments, the detectable reagent is at least one IRS-1/2 (Ser1101/Ser1149) antibody of the invention, and the sample or tissue is taken from a subject potentially having, or suspected of having, type 2 diabetes.

The further aspects, advantages, and embodiments of the invention are described in more detail below. All references cited herein are hereby incorporated by reference.

A. Antibodies and Cell Lines

IRS-1/2 phospho-specific antibodies of the invention bind to human IRS-1 only when phosphorylated at Ser1101 and/or to human IRS-2 only when phosphorylated at Ser1149, and do not substantially bind to IRS-1 or IRS-2 when not phosphorylated at these respective residues, nor to IRS-1 or IRS-2 when phosphorylated at other serine residues. The IRS-1/IRS-2 antibodies also bind highly homologous and equivalent IRS-1 and/or IRS-2 sites in other species, for example mouse IRS-1 (Ser1095) and/or IRS-2 (Ser1138), respectively, as disclosed herein. The IRS-1/2 antibodies of the invention include (a) monoclonal antibodies that bind phospho-IRS-1 (Ser1101) and/or phospho-IRS-2 (Ser 149), (b) polyclonal antibodies which bind to phospho-IRS-1 (Ser1101) and/or phospho-IRS-2 (Ser1149), and (c) antibodies (monoclonal or polyclonal) which specifically bind to the phospho-antigen (or more preferably the epitope) bound by the exemplary IRS-1/2(Ser1101/Ser1149) antibodies disclosed in the Examples herein, (d) antibodies as described in (a)-(c) above that bind equivalent phosphorylation IRS-1 and/or IRS-2 sites in other species (e.g. mouse, rat), as disclosed herein, and (e) fragments of (a), (b), (c), or (d) above which bind to the antigen (or more preferably the epitope) bound by the exemplary antibodies disclosed herein. Such antibodies and antibody fragments may be produced by a variety of techniques well known in the art, as discussed below. Antibodies that bind to the phosphorylated epitope (i.e., the specific binding site) bound by the exemplary IRS-1/2 (Ser1101/Ser1149) antibodies of the Examples herein can be identified in accordance with known techniques, such as their ability to compete with labeled IRS-1/2 antibodies in a competitive binding assay.

The preferred epitopic site of the human IRS-1/2 (Ser1101/Ser1149) antibodies of the invention is a peptide fragment consisting essentially of about 11 to 17 amino acids including the phosphorylated serine 1101 (in the case of IRS-1) or serine 1149 (in the case of IRS-2), wherein about 5 to 8 amino acids are positioned on each side of the serine phosphorylation site (for example, residues 1095-1108 of SEQ ID NO: 1, or residues 1143-1156 of SEQ ID NO: 2). This epitopic site, for example, corresponds to the following equivalent murine sites: residues 1089-1102 of SEQ ID NO: 3 (mouse IRS-1) (encompassing Ser1095) and residues 1132-1145 of SEQ ID NO: 4 (mouse IRS-2) (encompassing Ser1138).

The invention is not limited to IRS-1/2 antibodies, but includes equivalent molecules, such as protein binding domains or nucleic acid aptamers, which bind, in a phospho-specific manner, to essentially the same phosphorylated epitope to which the IRS-1/2 antibodies of the invention bind. See, e.g., Neuberger et al., *Nature* 312: 604 (1984). Such equivalent non-antibody reagents may be suitably employed in the methods of the invention further described below.

The term "antibody" or "antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrison et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed specific antibodies made according to the method disclosed in U.S. Pat. No. 4,676,980 (Segel et al.) The term "IRS-1/2 antibodies" is used interchangeably with the term "IRS-1/2 (Ser1101/Ser1149) antibodies" which means antibodies that specifically bind phospho-IRS-1 (Ser1101) and/or phospho-IRS-2 (Ser1149) (in the human sequence), both monoclonal and polyclonal, as disclosed herein. The term includes antibodies that bind equivalent and highly-homologous sites in IRS-1 and IRS-2 from other species, for example, murine IRS-1 (Ser1095) and/or IRS-2 (Ser1138). The term "does not bind" with respect to disclosed antibodies means does not substantially react with as compared to binding to phospho-IRS-1 and/or phospho-IRS-2. The term includes antibodies that bind whole protein comprising the target phosphorylation site, as well as shorter IRS-1 and/or IRS-2 polypeptides or fragments comprising the phosphorylated serine residue (e.g. a polypeptide of 5-25 or 25-50 or more residues comprising the target phosphorylation site).

The term "detectable reagent" means a molecule, including an antibody, peptide fragment, binding protein domain, etc., the binding of which to a desired target is detectable or traceable. Suitable means of detection are described below.

Polyclonal antibodies of the invention may be produced according to standard techniques by immunizing a suitable animal (e.g., rabbit, goat, etc.) with an antigen encompassing phospho-Ser1101 (equivalent to phospho-Ser1149), collecting immune serum from the animal, and separating the polyclonal antibodies from the immune serum, in accordance with known procedures. In a preferred embodiment, the antigen is a phospho-peptide antigen comprising the IRS-1/2 sequence surrounding and including phospho-Ser1101/1149, respectively, the antigen being selected and constructed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology,* 201: 264-283 (1991); Merrifield, *J. Am. Chem. Soc.* 85:21-49(1962)).

A particularly preferred peptide antigen, CRRRHS*SETFSST (SEQ ID NO: 11) (where *S=phosphoserine) is described in Example 1, below. It will be appreciated by those of skill in the art that longer or shorter phosphopeptide antigens may be employed. See Id. Polyclonal IRS-1/2 antibodies produced as described herein may be screened as further described below. This preferred antigen corresponds to the equivalent phosphorylation sites in murine IRS-1 and IRS-2 (see FIGS. 13 and 14, respectively).

Monoclonal antibodies of the invention may be produced in a hybridoma cell line according to the well-known technique of Kohler and Milstein. *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246:1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Natl. Acad. Sci.,* 82: 8653 (1985); Spira et al., *J. Immunol. Methods,* 74: 307 (1984)).

The invention also provides hybridoma clones, constructed as described above, that produce IRS-1/2 monoclonal antibodies of the invention. Similarly, the invention includes recombinant cells producing a phospho-IRS-1/2 (Ser1101/ Ser1149) antibody as disclosed herein, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

IRS-1/2 antibodies of the invention, whether polyclonal or monoclonal, may be screened for epitope and phospho-specificity according to standard techniques. See, e.g. Czernik et al., *Methods in Enzymology,* 201: 264-283 (1991). For example, the antibodies may be screened against the phospho and non-phospho peptide library by ELISA to ensure specificity for both the desired antigen (i.e. that epitope including Ser1101/Ser1149) and for reactivity only with the phosphorylated form of the antigen. Peptide competition assays may be carried out to confirm lack of reactivity with other IRS-1 and/or IRS-2 phosphoepitopes. The antibodies may also be tested by Western blotting against cell preparations containing IRS-1 and/or IRS-2, e.g. cell lines over-expressing IRS-1 and/or IRS-2, to confirm reactivity with the desired phosphorylated target. Specificity against the desired phosphorylated epitopes may also be examined by construction IRS-1/2 mutants lacking phosphorylatable residues at positions outside the desired epitope known to be phosphorylated, or by mutating the desired phospho-epitope and confirming lack of reactivity. IRS-1/2 antibodies of the invention may exhibit some limited cross-reactivity with non-IRS-1/2 epitopes. This is not unexpected as most antibodies exhibit some degree of crossreactivity, and anti-peptide antibodies will often cross-react with epitopes having high homology to the immunizing peptide. See, e.g., Czernik, supra. Cross-reactivity with non-IRS-1/2 proteins is readily characterized by Western blotting alongside markers of known molecular weight. Amino acid sequences of cross-reacting proteins may be examined to identify sites highly homologous to the IRS-1/2 sequence surrounding Ser1101/1149.

IRS-1/2 antibodies may be further characterized via immunohistochemical (IHC) staining using normal and diseased tissues to examine IRS-1/2 phosphorylation and activation status in diseased tissue. IHC may be carried out according to well-known techniques. See, e.g., ANTIBODIES: A LABORATORY MANUAL, Chapter 10, Harlow & Lane Eds., Cold Spring Harbor Laboratory (1988). Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

IRS-1 antibodies of the invention bind to human IRS-1 and/or IRS-2 when phosphorylated at the Ser1101 and/or Ser1149 site, respectively, but are not limited only to the human species, per se. Phospho-specific antibodies that bind conserved and highly-homologous phosphorylation sites in other species (e.g. mouse, rat, monkey, yeast), in addition to binding the human IRS-1/2 (pSer1101/pSer1149) sites, are within the scope of the present invention. For example, IRS-1/2 antibodies provided also bind the highly homologous Ser1095 and/or Ser1138 sites in mouse IRS-1 and IRS-2, respectively, as well as the homologous Ser1100 site in rat IRS-1 (SwissProt acc. no. P35570). Additional highly-homologous sites conserved in other species, which are in within the scope of the invention, can readily be identified by standard sequence comparisons, such as using BLAST, with the human IRS-1 and IRS-2 sites disclosed herein.

B. Detection & Profiling Methods

The methods disclosed herein may be employed with any biological sample potentially containing, or suspected of containing, phosphorylated IRS-1 and/or phosphorylated IRS-2. Biological samples taken from human subjects for use in the methods disclosed herein are generally biological fluids such as serum, blood plasma, fine needle aspirant, ductal lavage, bone marrow sample or ascites fluid. In the alternative, the sample taken from the subject can be a tissue sample (e.g., a biopsy tissue), such as bone marrow or tumor tissue, or a cell lysate, whether or not purified.

In one embodiment, the invention provides a method for detecting phosphorylated IRS-1/2 in a biological sample by (a) contacting a biological sample potentially (or suspected of) containing phosphorylated IRS-1 and/or phosphorylated IRS-2 with at least one detectable reagent that binds to IRS-1 and/or IRS-2 when phosphorylated at Ser1101 and/or Ser1149, respectively, under conditions suitable for formation of a reagent-IRS complex, and (b) detecting the presence of the complex in the sample, wherein the presence of the complex indicates the presence of phosphorylated IRS-1 (Ser1101) and/or phosphorylated IRS-2 (Ser1149) in the sample.

In a preferred embodiment, the reagent is an IRS-1/2 antibody of the invention. In other preferred embodiments, the biological sample has been contacted with at least one PKC inhibitor or a specific PKC theta inhibitor, or is obtained from a subject treated with such inhibitor. As disclosed herein (and discussed below) it has now been discovered that PKC theta phosphorylates IRS-1 at the serine1101 site. Accordingly, changes in IRS-1/2(Ser1101/Ser1149) phosphorylation resulting from contacting a biological sample with a test compound, such as a PKC inhibitor, may be examined to determine effect of such compound. The compound may be a "general" PKC inhibitor that inhibits more than one isoform of PKC (for example, bis-indoleimide), or may be a specific inhibitor of PKC theta. Exemplary inhibitors of PKC include, but are not limited to, Calphostin C, Chelerythrine chloride, Gö 6976, Ro-32-0432, Ro-31-7549, Ro-31-8220, Ro-31-8425, Ro-32-0432, and Rottlerin (commercially available from Calbiochem). Inhibitory compounds may be targeted inhibitors that modulate post-translational activity of PKC, or may be upstream expression inhibitors, such as siRNA or anti-sense inhibitors. In another preferred embodiment, the compound is being tested for inhibition of PKC activity or expression. Such compound may, for example, directly inhibit PKC activity, or may indirectly inhibit its activity by, e.g., inhibiting another kinase that phosphorylates and thus activates PKC.

Biological samples may be obtained from subjects at risk of, potentially, or suspected of, having a disease or condition involving altered IRS-1/2 expression or activity (e.g., Type 2 diabetes or obesity). For example, samples may be analyzed to monitor subjects who have been previously diagnosed as having diabetes, to screen subjects who have not been previously diagnosed as having diabetes, or to monitor the desirability or efficacy of therapeutics targeted at PKC isoforms, particularly PKC theta. In the case of type 2 diabetes, for example, the subjects will most frequently be adult males and females.

In another embodiment, the invention provides a method for profiling IRS-1 phosphorylation in a test tissue potentially having (or suspected of involving) altered IRS-1/2 activity, by (a) contacting the test tissue with at least one detectable reagent that binds to IRS-1 and/or IRS-2 when phosphorylated at Ser1101 and/or Ser1149, respectively, under conditions suitable for formation of a reagent-IRS complex, (b) detecting the presence of the complex in the test tissue, wherein the presence of the complex indicates the presence of phosphorylated IRS-1 (Ser1101) and/or phosphorylated IRS-2 (Ser1149) in the test tissue, and (c) comparing the presence of phosphorylated IRS-1 and/or IRS-2 detected in step(b) with the presence of phosphorylated IRS-1/2 (Ser1101/Ser1149) in a control tissue, wherein a difference in IRS-1/2 (Ser1101/1149) phosphorylation profiles between the test and control tissues indicates altered IRS-1 and/or IRS-2 activation in the test tissue. In a preferred embodiment, the reagent is a IRS-1/2 antibody of the invention. In other preferred embodiments, the test tissue is diabetic tissue potentially having (or suspected of involving) altered IRS-1/2 (Ser1101/Ser1149) phosphorylation.

The methods described above are applicable to examining tissues or samples from any disease or condition involving or characterized by altered IRS-1 and/or IRS-2 activity, particularly type 2 diabetes, in which phosphorylation of IRS-1 and/or IRS-2 at Ser1101/1149, respectively, (and possibly other serine residues) has predictive value as to the outcome of the disease or the response of the disease to therapy. It is anticipated that the IRS-1/2 antibodies will have diagnostic utility in a disease characterized by, or involving, altered insulin signaling, or IR or IRS-1/2 activity, or altered IRS-1/2 Ser1101/1149 phosphorylation. The methods are applicable, for example, where samples are taken from a subject has not been previously diagnosed as having type 2 diabetes, nor has yet undergone treatment for diabetes, and the method is employed to help diagnose the disease, or monitor the possible progression of the condition, or assess risk of the subject developing disease involving IRS-1/2 (Ser1101/1149) phosphorylation.

Such diagnostic assay may be carried out prior to preliminary blood evaluation or surgical surveillance procedures. Such a diagnostic assay may be employed to identify patients with activated or inhibited IRS-1 and/or IRS-2 who would be most likely to respond to diabetic therapeutics targeted at activating or inhibiting IRS-1/2 activity. Such a selection of patients would be useful in the clinical evaluation of efficacy of future IRS-1 and/or IRS-2-targeted therapeutics as well as in the future prescription of such drugs to patients. Alternatively, the methods are applicable where a subject has been previously diagnosed as having a disease involving altered insulin signaling, such as type 2 diabetes or obesity, and possibly has already undergone treatment for the disease, and the method is employed to monitor the progression of the disease involving IRS-1/2 (Ser1101/1149) phosphorylation, or the treatment thereof.

In another embodiment, the invention provides a method for identifying a compound which modulates phosphorylation of IRS-1/2 in a test tissue, by (a) contacting the test tissue with the compound, (b) detecting the level of phosphorylated IRS-1 and/or IRS-2 in said the test tissue of step (a) using at least one detectable reagent that binds to IRS1/2 when phosphorylated at Ser1101/Ser1149 under conditions suitable for formation of a reagent-IRS complex, and (c) comparing the level of phosphorylated IRS-1 and/or IRS-2 detected in step (b) with the presence of phosphorylated IRS-1/2 (Ser1101/1149) in a control tissue not contacted with the compound, wherein a difference in IRS-1/2 (Ser1101/1149) phosphorylation levels between the test and control tissues identifies the compound as a modulator of IRS-1/2 phosphorylation. In a preferred embodiment, the reagent is an IRS-1/2 antibody of the invention. In other preferred embodiments, the test tissue is a taken from a subject potentially (or suspected of) having type 2 diabetes and the compound is an IRS-1/2 activator. The compound may modulate IRS-1/2 activity either positively or negatively, for example by increasing or decreasing phosphorylation or expression of IRS-1/2. Alternatively, IRS-1/2 phosphorylation may be monitored to determine the efficacy of a compound targeted at any kinase that phosphorylates IRS-1 (Ser1101) and/or IRS-2 (Ser1149), for example PKC theta (as disclosed herein).

Conditions suitable for the formation of antibody-antigen complexes or reagent-IRS complexes are well known in the art (see part (d) below and references cited therein). It will be understood that more than one IRS-1/2 antibody may be used in the practice of the above-described methods. For example, a phospho-IRS-1/2 (Ser1101/Ser1149) antibody and a phospho-specific antibody to another serine, tyrosine, or threonine phosphorylation site may be simultaneously employed to detect phosphorylation of both sites in one step.

As presently disclosed, it has now been shown that PKC theta phosphorylates IRS-1 at the novel Ser1101 site identified herein. Due to high sequence homology, it is expected that this enzyme will also phosphorylate IRS-2 at Ser1149 (and/or equivalent sites in other species, such as mouse and rat). PKC theta activity is known to be increased in diabetic patients and insulin resistant animals (see Chalfant et al., supra.; Itani et al., supra.; Qu et al., supra.), and phosphorylation of IRS-1 at serine residues has been shown to correlate mostly with desensitization of the insulin stimulus (see Zick et al., supra.) Therefore, PKC theta phosphorylation of IRS-1 at Ser1101 and/or IRS-2 at Ser1149 may represent an important surrogate marker of insulin resistance, which develops as a consequence of Type 2 diabetes. Accordingly, the invention also provides methods for detecting PKC theta activity by assessing phosphorylation of IRS-1 (Ser1101) and/or IRS-2 (Ser1149).

In one embodiment, the invention provides a method for detecting PKC theta activity in a biological sample by (a) contacting a biological with at least one detectable reagent that binds to IRS-1 and/or IRS-2 when phosphorylated at Ser1101 or Ser1149, respectively, under conditions suitable for formation of a reagent-IRS complex, and (b) detecting the presence of the complex in the sample, wherein the presence of the complex indicates the presence of PKC theta activity in the sample. The method may further include the step of (c) comparing the presence of phosphorylated IRS-1 and/or IRS-2 detected in step (b) with the presence of phosphorylated IRS-1 (Ser1101) in a control tissue having known PKC theta activity, wherein a difference in IRS-1 (Ser1101) phosphorylation profiles between the test and control tissues indicates altered PKC theta activity in the test tissue.

In a preferred embodiment, the reagent is an IRS-1/2 antibody of the invention. Biological samples may be obtained from subjects at risk of, potentially, or suspected of having a disease or condition involving or characterized by altered PKC theta expression or activity (e.g., Type 2 diabetes, as in a preferred embodiment). For example, samples may be analyzed to monitor subjects who have been previously diagnosed as having diabetes, to screen subjects who have not been previously diagnosed as having diabetes, or to monitor the desirability or efficacy of therapeutics targeted at PKC theta. In one preferred embodiment, the biological sample has been contacted with at least one PKC inhibitor or PKC theta inhibitor, or is obtained from a subject treated with such inhibitor. Such inhibitors (discussed above) may be test compounds not yet known to in fact inhibit PKC and are being tested for their ability to inhibit PKC activity or expression. Alternatively, they may be compounds known, or anticipated to, so inhibit PKC.

In another embodiment, the invention provides a method for profiling PKC theta activity in a test tissue, by (a) contacting the test tissue with at least one detectable reagent that binds to IRS-1 and/or IRS-2 when phosphorylated at Ser1101 and/or Ser1149, respectively, under conditions suitable for formation of a reagent-IRS complex, (b) detecting the presence of the complex in the test tissue, wherein the presence of the complex indicates the presence of phosphorylated IRS-1 (Ser1101) and/or IRS-2 (Ser1149) in the test tissue, and (c) comparing the presence of phosphorylated IRS-1 and/or IRS-2 detected in step (b) with the presence of phosphorylated IRS-1 (Ser1101) and/or IRS-2(Ser1149) in a control tissue having known PKC theta activity, wherein a difference in IRS-1/2 (Ser1101/Ser1149) phosphorylation profiles between the test and control tissues indicates altered PKC theta activity in the test tissue. In a preferred embodiment, the reagent is an IRS-1 antibody of the invention. In other preferred embodiments, the test tissue is diabetic tissue suspected of involving altered PKC theta activity.

The methods described above are applicable to examining tissues or samples from any disease or condition involving or characterized by altered PKC theta activity, particularly type 2 diabetes, in which phosphorylation of IRS-1 at Ser1101 and/or IRS-2 at Ser1149 (and both possibly other serine residues) by PKC theta has predictive value as to the outcome of the disease or the response of the disease to therapy. It is anticipated that the IRS-1 antibodies described herein will have diagnostic utility in a disease characterized by, or involving, altered PKC theta activity, and hence resultant altered IRS-1 Ser1101 and/or IRS-2 Ser1149 phosphorylation.

The methods are applicable, for example, where samples are taken from a subject that has not been previously diagnosed as having type 2 diabetes, nor has yet undergone treatment for diabetes, and the method is employed to help diagnose the disease, or monitor the possible progression of the condition, or assess risk of the subject developing the disease. Such diagnostic assay may be carried out prior to preliminary blood evaluation or surgical surveillance procedures. The diagnostic assay may be employed to identify patients with activated or inhibited PKC theta who would be most likely to respond to therapeutics targeted at activating or inhibiting, respectively, PKC theta activity upon IRS-1/2 (Ser1101/Ser1149). Such a selection of patients would be useful in the clinical evaluation of efficacy of future PKC theta targeted therapeutics as well as in the future prescription of such drugs to patients. Alternatively, the methods are applicable where a subject has been previously diagnosed as having a disease involving altered PKC theta activity, such as type 2 diabetes, and possibly has already undergone treatment for the disease, and the method is employed to monitor the progression of the disease by monitoring IRS-1 (Ser1101) phosphorylation and/or IRS-2 (Ser1149) phosphorylation, or the treatment thereof.

In another embodiment, the invention provides a method for identifying a compound which modulates PKC theta activity in a test tissue, by (a) contacting the test tissue with the compound, (b) detecting the level of phosphorylated IRS-1/2 in said test tissue of step (a) using at least one detectable reagent that binds to IRS-1 and/or IRS-2 when phosphorylated at Ser1101 and/or Ser1149, respectively, under conditions suitable for formation of a reagent-IRS complex, and (c) comparing the level of phosphorylated IRS-1/2 detected in step(b) with the presence of phosphorylated IRS-1 (Ser1101) and/or IRS-2 (Ser1149) in a control tissue not contacted with the compound having known PKC theta activity, wherein a difference in IRS-1/2 (Ser1101/Ser1149) phosphorylation levels between the test and control tissues identifies the compound as a modulator of PKC theta activity. In a preferred embodiment, the reagent is an IRS-1 antibody of the invention. In other preferred embodiments, the test tissue is a taken from a subject suspected of having type 2 diabetes and the compound is a PKC theta inhibitor.

The compound may modulate PKC theta activity either positively or negatively, for example by increasing or decreasing phosphorylation or expression of IRS-1 and/or IRS-2. IRS-1 (Ser1101) phosphorylation and activity may be monitored, for example, to determine the efficacy of an anti-PKC theta therapeutic, e.g. a PKC theta inhibitor. Alternatively, IRS-1 (Ser1101) and/or IRS-2 (Ser1149) phosphorylation may be monitored to determine the efficacy of a compound targeted at any kinase that activates or inhibits PKC theta.

C. Immunoassay Formats & Diagnostic Kits

Assays carried out in accordance with methods of the present invention may be homogeneous assays or heterogeneous assays. In a homogeneous assay the immunological reaction usually involves a IRS1/2-specific reagent (e.g. a IRS-1/2 antibody of the invention), a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radioisotopes, fluorescent dyes, enzymes, bacteriophages, coenzymes, and so forth.

In a heterogeneous assay approach, the reagents are usually the specimen, an IRS-1/2-specific reagent (e.g., the IRS-1/2 antibody of the invention), and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-1 inked immunoassays, and the like.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well described. See id. Monoclonal antibodies of the invention may be used in a "two-site" or "sandwich" assay, with a single cell line serving as a source for both the labeled monoclonal antibody and the bound monoclonal antibody. Such assays are described in U.S. Pat. No. 4,376,110. The concentration of detectable reagent should be sufficient such that the binding of phosphorylated IRS-1 is detectable compared to background.

IRS-1/2 antibodies disclosed herein may be conjugated to a solid support suitable for a diagnostic assay (e.g., beads, plates, slides or wells formed from materials such as latex or polystyrene) in accordance with known techniques, such as precipitation. Antibodies of the invention, or other IRS-1 binding reagents, may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

IRS-1/2 antibodies of the invention may also be used in a flow cytometry assay to determine the activation status of IRS-1/2 in patients before, during, and after treatment with a drug targeted at inhibiting IRS1/2 phosphorylation at Ser1101/1149. Inhibitors of PKC theta are one example of such phosphorylation inhibitors. For example, bone marrow cells or peripheral blood cells from patients may be analyzed by flow cytometry for IRS-1/2 phosphorylation, as well as for markers identifying various hematopoietic cell types. In this manner, IRS-1/2 activation status of the diseased cells may be specifically characterized. Flow cytometry may be carried out according to standard methods. See, e.g. Chow et al., Cytometry (*Communications in Clinical Cytometry*) 46:72-78 (2001). Briefly and by way of example, the following protocol for cytometric analysis may be employed: fixation of the cells with 2% paraformaldehyde for 20 minutes at 37° C. followed by permeabilization in 90% methanol for 30 minutes on ice. Cells may then be stained with the primary IRS-1 antibody, washed and labeled with a fluorescent-labeled secondary antibody. The cells would then be analyzed on a flow cytometer (e.g. a Beckman Coulter EPICS-XL) according to the specific protocols of the instrument used. Such an analysis would identify the presence of phosphorylated IRS-1 and/or IRS-2 in a cell of interest and reveal the drug response on the targeted IRS-1 protein or kinase (e.g. PKC theta).

Diagnostic kits for carrying out the methods disclosed above are also provided by the invention. Such kits comprise at least one detectable reagent that binds to IRS-1 and/or IRS-2 when phosphorylated at Ser 1101 and/or Ser 1149, respectively. In a preferred embodiment, the reagent is an IRS-1/2 antibody of the invention. In one embodiment, the invention provides a kit for the detection of phosphorylated IRS-1 (Ser 1101) and/or IRS-2 (Ser 1149) in a biological sample comprising (a) at least one IRS-1/2 antibody of the invention (e.g., a phospho-specific antibody that binds phospho-IRS-1/2 (Ser 1101/Ser 1149)) and (b) at least one secondary antibody conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like.

In another embodiment, the invention provides a kit for the detection of PKC theta activity in a biological sample comprising (a) at least one IRS-1/2 antibody of the invention (e.g., a phospho-specific antibody that binds phospho-IRS-1 (Ser 1101) and/or phospho-IRS-2 (Ser 1149) and (b) at least one secondary antibody conjugated to a detectable group. Ancillary agents as described above may likewise be included. The test kit may be packaged in any suitable manner, typically with all elements in a single container along with a sheet of printed instructions for carrying out the test.

The following Examples are provided only to further illustrate the invention, and are not intended to limit its scope, except as provided in the claims appended hereto. The present invention encompasses modifications and variations of the methods taught herein which would be obvious to one of ordinary skill in the art.

EXAMPLE 1

Production of an IRS-1/2 (Ser1101/Ser1149)
Phospho-specific Antibody

A previously unknown IRS-1 phosphorylation site, serine 1101, was identified as described above by predictive analysis of the human IRS-1 protein sequence using the ScanSite program. Yaffe et al., supra. A 13 amino acid phospho-peptide antigen, CRRRHS*SETFSST (SEQ ID NO: 11) (where *S=phosphoserine), corresponding to residues 1095-1107 of human IRS-1 (see SEQ ID NO: 1), was constructed according to standard synthesis techniques using a Rainin/Protein Technologies, Inc., Symphony peptide synthesizer. See ANTIBODIES: A LABORATORY MANUAL, supra.; Merrifield, supra. This peptide antigen also corresponds to highly homologous residues 1143-1155 of human IRS-2 (see SEQ ID NO: 2) (as well as the highly homologous sites in murine IRS-1 and IRS-2; see FIGS. 13-14).

This peptide was coupled to KLH, and rabbits were injected intradermally (ID) on back with antigen in complete Freunds adjuvant (500 μg antigen per rabbit). The rabbits were boosted with same antigen in incomplete Freund adjuvant (250 μg antigen per rabbit) every three weeks. After the fifth boost, the bleeds were collected. The sera were purified by Protein A-sepharose affinity chromatography as previously described (see ANTIBODIES: A LABORATORY MANUAL, Cold Spring Harbor, supra.). Further purification steps were performed using adsorption of non-specific material to nonphosphopeptide affinity column, followed by elution of reactive material from a phosphopeptide affinity column at low pH, as follows. The eluted immunoglobulins were loaded onto CRRRHSSETFSST-resin Knotes column. The flow through fraction was collected and applied onto CRRRHS*SETFSST-resin column. After washing the column extensively, the phospho-IRS-1/2 (Ser1101/Ser1149) antibodies were eluted, dialyzed, and kept in antibody storage buffer.

Antibodies were characterized by ELISA against phospho- and nonphosphopeptides to determine the extent of phospho-specificity and by Western blotting to examine specificity against whole cell extracts, as described in detail below.

Characterization of p-IRS-1/2 (Ser1101/Ser1149) Antibodies Against Phosphorylated Ser1101 and Ser1149, in Human IRS-1/2.

To characterize the polyclonal antibodies raised against the phosphorylated peptide described above, Western blots with three cell types were used: NIH3T3 L1 differentiated adipocytes, L6 differentiated myocytes and CHO cells overexpressing the insulin receptor and IRS-1. The different cell types were stimulated with insulin, TPA, PDGF and TNF α, all factors known to induce serine phosphorylation of IRS-1 through the activation of different pathways.

FIG. 3 shows the time course of phosphorylation of IRS-1 at Ser1101, Ser 330, and Ser307 upon stimulation with insulin in CHO cells overexpressing IRS-1 and the insulin receptor. Phosphorylation of a previously described site in IRS1, Ser612, as well as activation of the Akt and MAPK pathways is shown to follow the same induction kinetics as Ser 101, 307 and 330. Since fat and muscle tissues are among the most important insulin responsive tissues in the body, phosphorylation of IRS-1 at Ser 101, 330 and 307 in adipocytes and myocytes was further examined. 3T3 L1 adipocytes were treated with insulin for 5 and 30 minutes and L6 myocytes were treated with TNF α and insulin for 15 minutes. IRS-1 was immunoprecipitated and immunoblotted with phospho-IRS1 antibodies against Ser1101, Ser330 (only in muscle cells) and Ser307, as well as total IRS-1 antibodies.

The results shown in FIGS. 4 and 5 demonstrate that Ser1101 is phosphorylated by insulin treatment (fat and muscle cells) and by TNF α treatment (muscle cells). Upon insulin treatment phosphorylation at Ser307 occurred in both cell types, but at Ser330 only in myocytes, whereas both sites were not affected by TNF α treatment. Analysis of total IRS1 protein and phosphotyrosine-IRS-1 served as controls to indicate equal loading and to verify that the stimuli applied worked as expected.

To determine the specificity of the IRS-1/2 phospho (Ser1101/Ser1149) antibodies, expression constructs encoding epitope (HA) tagged wild-type IRS-1 protein, or IRS-1 containing an alanine substitution at position 1101 were transfected to NIH 3T3 cells, according to standard methods (See Qiagen Polyfect® Transfection Reagent Handbook, September 2000).

These cell were stimulated with insulin and HA-IRS-1 proteins were immunoprecipitated using an anti-HA antibody. The immunoprecipitated material was then immunoblotted using the phospho-IRS-1/2 antibody. FIG. 6 shows that the phospho IRS-1/2 (Ser1101/Ser1149) antibody detected the wild-type protein, but failed to detected IRS-1 when Ser1101 was mutated to alanine. This demonstrates that the phospho IRS-1/2 antibody recognizes specifically phosphorylated Ser1101 in IRS-1. Anti-HA antibodies were used to control for the amounts of total IRS-1 protein immunoprecipitated and immunoblotted in this experiments, and phosphotyrosine immunoblot indicated that the insulin treatment worked as expected leading to tyrosine phosphorylation of IRS-1.

We next examined whether IRS-1 phosphorylation at Ser1101 would correlate with the insulin resistance state that typically occurs in obese Zucker rats. Total IRS-1 protein was immunoprecipitated from liver extracts of lean or obese Zucker rats, and immunoblotted with the phospho-IRS-1 Ser1101 antibody. FIG. 7 shows an increased level of phosphorylation of IRS-1 at Ser1101 in the liver of obese, but not lean Zucker rats. These results suggests that phosphorylation of IRS-1 at Ser1101 is a marker of obesity-induced insulin resistance.

Because of the high homology (and near identity) between the Ser1101 site in IRS-1 and Ser1149 site in IRS-2, the ability of polyclonal antibodies raised against the phosphorylated peptide to also detect the homologous phosphorylated Ser1149 in IRS-2 was examined, using a CHO cell line overexpressing the IRS-2 protein. FIG. 8 shows that insulin stimulated the phosphorylation of IRS-2 at Ser1149 reaching maximal levels after one hour of exposure to insulin. These results indicate that the phospho-IRS-1/2 antibodies also specifically detect IRS-2 when phosphorylated at Ser1149. The antibodies also bind the highly homologous and equivalent Ser1095 and Ser 1138 sites in mouse IRS-1 and IRS-2, respectively, and the equivalent IRS-1 (Ser1100) site in rats.

EXAMPLE 2

Phosphorylation of IRS-1 (Ser1101) by Protein Kinase C theta

In order to analyze the potential signaling pathways leading to phosphorylation of Ser 101, CHO-IR/IRS-1 cells were stimulated with insulin, PDGF and with the activator of protein kinase C, TPA, and IRS-1 proteins were immunoprecipitated with a specific IRS-1 antibody followed by immunoblotting with the IRS-1/2 (Ser1101/Ser1449) phospho-antibodies described in Example 1. FIG. 9 shows a robust induction of phosphorylation at Ser1101, particularly upon PKC activation (left panel). As expected, only insulin treatment induced tyrosine phosphorylation of the insulin receptor and IRS-1 (right panel), but all treatments induced MAPK and phosphorylation of PKCs. Also, as previously reported, only insulin and PDGF induced the activation of Akt. This results suggest that despite being selected as an Akt site by ScanSite, Ser1101 is not dependent on Akt activation, but most likely on PKC activation. This is supported by the fact that phosphorylation at Ser1101 is inhibited by the PKC inhibitor Bisindoleimide, but not by inhibitors of the PI3K/Akt pathway, wortmannin and LY294002 (FIG. 10).

Insulin-dependent phosphorylation of IRS-1 at Ser1101 is also not affected by inhibitors of the MEK/MAPK pathway (PD98059), PKA and MSK1 kinases (H89), CaM kinases (KN62), Src tyrosine kinases (Genistein and PP2). Ser1101 is somewhat reduced by SU6686, an inhibitor of the insulin receptor tyrosine kinase (FIG. 10). The results indicate that upon different types of stimuli, insulin, PDGF, TNF-α, TPA, etc., IRS-1 becomes phosphorylated at the previously unknown site Ser1101, as well as Ser307 and Ser330. In the case of Ser1101, the evidence indicates a PKC isoform being involved as the kinase directly phosphorylating Ser1101 or participating in the pathway leading to Ser1101 phosphorylation. Multiple lines of evidence have suggested that isoform-selective activation of PKC phosphorylates and downregulates IRS-1, or other components of the insulin pathway. The strong link between insulin resistance and increased lipid availability has led to the proposal that accumulation of lipid metabolites, via activation of protein kinase C leads to dysregulated insulin signaling (see Pan et al., *Diabetes* 46: 983-988 (1997)). Recent studies have linked an increased amount and activities of certain PKC isoforms, particularly PKC theta, in skeletal muscle of insulin resistant human patients and of insulin-resistant obese Zucker rats (see, Itani et al., supra.; Qu et al., supra.; Chalfant et al., supra.)

However, despite the fact that Ser1101 was predicted by ScanSite as an Akt substrate, the results shown in FIGS. 9 & 10 suggest that Akt cannot phosphorylate this site in vivo. Accordingly, the phosphorylation of IRS-1 (Ser1101) by PKC theta and Akt in vitro was examined. Kinase reactions were performed with active Akt and multiple PKC isoform kinases using a GST-IRS-1 C-terminal fragment containing IRS-1 and full-length IRS-1 pulled down from unstimulated CHO-IR/IRS-1 cells. As shown in FIG. 11, PKC theta is the only PKC isoform that robustly phosphorylated the GST-IRS-1 fusion protein substrate at Ser1101. The Akt kinase could not effectively phosphorylate IRS-1 at Ser1101, despite the occurrence of this residue within a putative Akt motif. This result demonstrates that Ser1101 is a substrate of PKC theta in vitro.

To verify whether PKC theta controls phosphorylation of IRS-1 Ser1101 in vivo, HA-tagged IRS-1 wild-type expression constructs were co-transfected (according to standard methods, see Qiagen Polyfect® Handbook, supra.) with constructs expressing a constitutively activated version of PKC theta and a dominant negative PKC theta mutant. FIG. 12 shows that constitutively activate PKC theta induced the phosphorylation of IRS-1 at Ser1101 without the need of insulin stimulation. PKC theta induced phosphorylation of IRS-1 Ser1101 also correlated with a reduction in tyrosine phosphorylation of IRS-1, which is indicative of IRS-1 inactivation. Consistently, dominant negative PKC theta blocked insulin-induced phosphorylation of IRS-1 at Ser1101. Altogether the combined results shown in FIGS. 8-11 demonstrate that the IRS-1 Ser1101 site is substrate of PKC theta in vitro and in vivo. Given the near-identity of the corresponding IRS-1 Ser1149, it is expected that this site will also be a substrate of PKC theta (as well as equivalent sites in other species such as rat, mice). These results indicate that Ser1101 (and Ser1149) represents a novel marker of PKC theta activity in samples from insulin resistant patients and a marker to monitor the activity of PKC theta specific inhibitors, which could potentially be used to treat insulin resistance.

EXAMPLE 3

Production of an IRS-1/2 (Ser1101/Ser1149) Phospho-specific Monoclonal Antibody

Phospho-IRS-1/2(Ser1101/Ser1149)-specific monoclonal antibodies may be produced from spleen cells of the immunized BALB/c mouse described in Example 1, above, following standard procedures (Harlow and Lane, 1988). Briefly, the mouse spleen is fused to SP2/0 mouse myeloma fusion partner cells according to the protocol of Kohler and Milstein (1975). Colonies originating from the fusion are screened by ELISA for reactivity to the phospho-peptide and non-phospho-peptide and by Western blot analysis. Colonies found to be positive by ELISA to the phospho-peptide while negative to the non-phospho-peptide may be further characterized by Western blot analysis. Colonies found to be positive by Western blot analysis are then subcloned by limited dilution. Mouse ascites are produced from positive clones obtained from subcloning. Clones are selected for phospho-specificity by ELISA and by Western blot analysis using cell culture supernatant. Selected positive clones are then subcloned to produce final desired clones producing phospho-IRS-1/2 (Ser1101/Ser1149)-specific monoclonal antibodies.

Ascites fluid from clones obtained from the IRS-1/2 fusion may be further tested by Western blot analysis. The ascites fluid will likely give similar results on Western blot analysis as observed with the cell culture supernatant, indicating phospho-specificity on IRS-1/2-induced 3T3L1 adipocytes and/or L6 differentiated myocyte cells, for example.

What is claimed is:

1. An isolated Insulin Receptor Substrate-1/2 phospho-specific antibody that binds to human Insulin Receptor Substrate-1 (IRS-1) when phosphorylated at serine 1101 (SEQ ID NO: 1), but does not bind human IRS-1 when not phosphorylated at serine 1101.

2. The antibody of claim 1, wherein said antibody further binds to human Insulin Receptor Substrate-2 (IRS-2) when phosphorylated at serine 1149 (SEQ ID NO: 2), but does not bind human IRS-2 when not phosphorylated at serine 1149.

3. The antibody of claim 1, wherein said antibody further binds to murine IRS-1 when phosphorylated at serine 1095 (SEQ ID NO: 3), but does not bind murine IRS-1 when not phosphorylated at serine 1095.

4. The antibody of claim 1, wherein said antibody further binds to murine IRS-2 when phosphorylated at serine 1138 (SEQ ID NO: 4), but does not bind murine IRS-2 when not phosphorylated at serine 1138.

5. An isolated Insulin Receptor Substrate-1/2 phospho-specific antibody that binds to human IRS-2 when phosphorylated at serine 1149 (SEQ ID NO: 2), but does not bind human IRS-2 when not phosphorylated at serine 1149.

6. The antibody of claim 5, wherein said antibody further binds to human IRS-1 when phosphorylated at serine 1101 (SEQ ID NO: 1), but does not bind human IRS-1 when not phosphorylated at serine 1101.

7. The antibody of claim 5, wherein said antibody further binds to murine IRS-1 when phosphorylated at serine 1095 (SEQ ID NO: 3), but does not bind murine IRS-1 when not phosphorylated at serine 1095.

8. The antibody of claim 5 wherein, said antibody further binds to murine IRS-2 when phosphorylated at serine 1138 (SEQ ID NO: 4), but does not bind murine IRS-2 when not phosphorylated at serine 1138.

9. An isolated Insulin Receptor Substrate-1/2 phospho-specific antibody that binds to murine IRS-1 when phosphorylated at serine 1095 (SEQ ID NO: 3), but does not bind murine IRS-1 when not phosphorylated at serine 1095.

10. The antibody of claim 9, wherein said antibody further binds to human IRS-1 when phosphorylated at serine 1101 (SEQ ID NO: 1), but does not bind human IRS-1 when not phosphorylated at serine 1101.

11. The antibody of claim 9, wherein said antibody further binds to human IRS-2 when phosphorylated at serine 1149 (SEQ ID NO: 2), but does not bind human IRS-2 when not phosphorylated at serine 1149.

12. The antibody of claim 9, wherein said antibody further binds to murine IRS-2 when phosphorylated at serine 1138 (SEQ ID NO: 4), but does not bind murine IRS-2 when not phosphorylated at serine 1138.

13. An isolated Insulin Receptor Substrate-1/2 specific antibody that binds to murine IRS-2 when phosphorylated at serine 1138 (SEQ ID NO: 4), but does not bind murine IRS-2 when not phosphorylated at serine 1138.

14. The antibody of claim 13, wherein said antibody further binds to human IRS-1 when phosphorylated at serine 1101 (SEQ ID NO: 1), but does not bind human IRS-1 when not phosphorylated at serine 1101.

15. The antibody of claim 13, wherein said antibody further binds to human IRS-2 when phosphorylated at serine 1149 (SEQ ID NO: 2), but does not bind human IRS-2 when not phosphorylated at serine 1149.

16. The antibody of claim 13, wherein said antibody further binds to murine IRS-1 when phosphorylated at serine 1095 (SEQ ID NO: 3), but does not bind murine IRS-1 when not phosphorylated at serine 1095.

17. The antibody as in one of claims 1, 5, 9 or 13, wherein said antibody is polyclonal.

18. The antibody as in one of claims 1, 5, 9 or 13, wherein said antibody is monoclonal.

19. A hybridoma cell line producing any one of the antibodies of claim 18.

20. A kit for the detection of phosphorylated human IRS-1 (Ser 1101) (SEQ ID NO: 1) in a biological sample, said kit comprising (a) the antibody of claim 1 and (b) at least one secondary antibody conjugated to a detectable group.

21. A kit for the detection of phosphorylated human IRS-2 (Ser 1149) (SEQ ID NO: 2) in a biological sample, said kit comprising (a) the antibody of claim 5 and (b) at least one secondary antibody conjugated to a detectable group.

22. A kit for the detection of PKC theta activity in a biological sample, said kit comprising (a) at least one antibody of claims 1, or 5 and (b) at least one secondary antibody conjugated to a detectable group.

* * * * *

SEQUENCE LISTING

<160> NUMBER OF SEQ ID NOS: 11

<210> SEQ ID NO 1
<211> LENGTH: 1242
<212> TYPE: PRT
<213> ORGANISM: Homo sapiens

<400> SEQUENCE: 1

Met Ala Ser Pro Pro Glu Ser Asp Gly Phe Ser Asp Val Arg Lys Val
1               5                   10                  15

Gly Tyr Leu Arg Lys Pro Lys Ser Met His Lys Arg Phe Phe Val Leu
            20                  25                  30

-continued

```
Arg Ala Ala Ser Glu Ala Gly Gly Pro Ala Arg Leu Glu Tyr Tyr Glu
             35                  40                  45

Asn Glu Lys Lys Trp Arg His Lys Ser Ser Ala Pro Lys Arg Ser Ile
 50                  55                  60

Pro Leu Glu Ser Cys Phe Asn Ile Asn Lys Arg Ala Asp Ser Lys Asn
 65                  70                  75                  80

Lys His Leu Val Ala Leu Tyr Thr Arg Asp Glu His Phe Ala Ile Ala
             85                  90                  95

Ala Asp Ser Glu Ala Glu Gln Asp Ser Trp Tyr Gln Ala Leu Leu Gln
            100                 105                 110

Leu His Asn Arg Ala Lys Gly His His Asp Gly Ala Ala Leu Gly
            115                 120                 125

Ala Gly Gly Gly Gly Ser Cys Ser Gly Ser Gly Leu Gly Glu
            130                 135             140

Ala Gly Glu Asp Leu Ser Tyr Gly Asp Val Pro Pro Gly Pro Ala Phe
145                 150                 155                 160

Lys Glu Val Trp Gln Val Ile Leu Lys Pro Lys Gly Leu Gly Gln Thr
                165                 170                 175

Lys Asn Leu Ile Gly Ile Tyr Arg Leu Cys Leu Thr Ser Lys Thr Ile
                180                 185                 190

Ser Phe Val Lys Leu Asn Ser Glu Ala Ala Val Val Leu Gln Leu
            195                 200                 205

Met Asn Ile Arg Arg Cys Gly His Ser Glu Asn Phe Phe Ile Glu
        210                 215                 220

Val Gly Arg Ser Ala Val Thr Gly Pro Gly Glu Phe Trp Met Gln Val
225                 230                 235                 240

Asp Asp Ser Val Val Ala Gln Asn Met His Glu Thr Ile Leu Glu Ala
                245                 250                 255

Met Arg Ala Met Ser Asp Glu Phe Arg Pro Arg Ser Lys Ser Gln Ser
            260                 265                 270

Ser Ser Asn Cys Ser Asn Pro Ile Ser Val Pro Leu Arg Arg His His
        275                 280                 285

Leu Asn Asn Pro Pro Ser Gln Val Gly Leu Thr Arg Arg Ser Arg
        290                 295                 300

Thr Glu Ser Ile Thr Ala Thr Ser Pro Ala Ser Met Val Gly Gly Lys
305                 310                 315                 320

Pro Gly Ser Phe Arg Val Arg Ala Ser Ser Asp Gly Glu Gly Thr Met
                325                 330                 335

Ser Arg Pro Ala Ser Val Asp Gly Ser Pro Val Ser Pro Ser Thr Asn
            340                 345                 350

Arg Thr His Ala His Arg His Arg Gly Ser Ala Arg Leu His Pro Pro
            355                 360                 365

Leu Asn His Ser Arg Ser Ile Pro Met Pro Ala Ser Arg Cys Ser Pro
        370                 375                 380

Ser Ala Thr Ser Pro Val Ser Leu Ser Ser Ser Thr Ser Gly His
385                 390                 395                 400

Gly Ser Thr Ser Asp Cys Leu Phe Pro Arg Arg Ser Ala Ser Val
            405                 410                 415

Ser Gly Ser Pro Ser Asp Gly Gly Phe Ile Ser Ser Asp Glu Tyr Gly
            420                 425                 430

Ser Ser Pro Cys Asp Phe Arg Ser Ser Phe Arg Ser Val Thr Pro Asp
        435                 440                 445
```

```
Ser Leu Gly His Thr Pro Pro Ala Arg Gly Glu Glu Leu Ser Asn
    450                 455                 460

Tyr Ile Cys Met Gly Gly Lys Gly Pro Ser Thr Leu Thr Ala Pro Asn
465                 470                 475                 480

Gly His Tyr Ile Leu Ser Arg Gly Gly Asn Gly His Arg Cys Thr Pro
                    485                 490                 495

Gly Thr Gly Leu Gly Thr Ser Pro Ala Leu Ala Gly Asp Glu Ala Ala
                500                 505                 510

Ser Ala Ala Asp Leu Asp Asn Arg Phe Arg Lys Arg Thr His Ser Ala
                515                 520                 525

Gly Thr Ser Pro Thr Ile Thr His Gln Lys Thr Pro Ser Gln Ser Ser
    530                 535                 540

Val Ala Ser Ile Glu Glu Tyr Thr Glu Met Met Pro Ala Tyr Pro Pro
545                 550                 555                 560

Gly Gly Gly Ser Gly Gly Arg Leu Pro Gly His Arg His Ser Ala Phe
                565                 570                 575

Val Pro Thr Arg Ser Tyr Pro Glu Glu Gly Leu Glu Met His Pro Leu
                580                 585                 590

Glu Arg Arg Gly Gly His His Arg Pro Asp Ser Ser Thr Leu His Thr
                595                 600                 605

Asp Asp Gly Tyr Met Pro Met Ser Pro Gly Val Ala Pro Val Pro Ser
    610                 615                 620

Gly Arg Lys Gly Ser Gly Asp Tyr Met Pro Met Ser Pro Lys Ser Val
625                 630                 635                 640

Ser Ala Pro Gln Gln Ile Ile Asn Pro Ile Arg Arg His Pro Gln Arg
                645                 650                 655

Val Asp Pro Asn Gly Tyr Met Met Met Ser Pro Ser Gly Gly Cys Ser
                660                 665                 670

Pro Asp Ile Gly Gly Gly Pro Ser Ser Ser Ser Ser Ser Asn Ala
                675                 680                 685

Val Pro Ser Gly Thr Ser Tyr Gly Lys Leu Trp Thr Asn Gly Val Gly
    690                 695                 700

Gly His His Ser His Val Leu Pro His Pro Lys Pro Pro Val Glu Ser
705                 710                 715                 720

Ser Gly Gly Lys Leu Leu Pro Cys Thr Gly Asp Tyr Met Asn Met Ser
                725                 730                 735

Pro Val Gly Asp Ser Asn Thr Ser Ser Pro Ser Asp Cys Tyr Tyr Gly
                740                 745                 750

Pro Glu Asp Pro Gln His Lys Pro Val Leu Ser Tyr Tyr Ser Leu Pro
                755                 760                 765

Arg Ser Phe Lys His Thr Gln Arg Pro Gly Glu Pro Glu Glu Gly Ala
    770                 775                 780

Arg His Gln His Leu Arg Leu Ser Thr Ser Ser Gly Arg Leu Leu Tyr
785                 790                 795                 800

Ala Ala Thr Ala Asp Asp Ser Ser Ser Thr Ser Ser Asp Ser Leu
                805                 810                 815

Gly Gly Gly Tyr Cys Gly Ala Arg Leu Glu Pro Ser Leu Pro His Pro
                820                 825                 830

His His Gln Val Leu Gln Pro His Leu Pro Arg Lys Val Asp Thr Ala
                835                 840                 845

Ala Gln Thr Asn Ser Arg Leu Ala Arg Pro Thr Arg Leu Ser Leu Gly
    850                 855                 860

Asp Pro Lys Ala Ser Thr Leu Pro Arg Ala Arg Glu Gln Gln Gln Gln
```

-continued

```
                865                 870                 875                 880
        Gln Gln Pro Leu Leu His Pro Pro Glu Pro Lys Ser Pro Gly Glu Tyr
                        885                 890                 895

Val Asn Ile Glu Phe Gly Ser Asp Gln Ser Gly Tyr Leu Ser Gly Pro
                    900                 905                 910

Val Ala Phe His Ser Ser Pro Ser Val Arg Cys Pro Ser Gln Leu Gln
                915                 920                 925

Pro Ala Pro Arg Glu Glu Thr Gly Thr Glu Glu Tyr Met Lys Met
            930                 935                 940

Asp Leu Gly Pro Gly Arg Arg Ala Ala Trp Gln Glu Ser Thr Gly Val
        945                 950                 955                 960

Glu Met Gly Arg Leu Gly Pro Ala Pro Pro Gly Ala Ala Ser Ile Cys
                        965                 970                 975

Arg Pro Thr Arg Ala Val Pro Ser Ser Arg Gly Asp Tyr Met Thr Met
                    980                 985                 990

Gln Met Ser Cys Pro Arg Gln Ser  Tyr Val Asp Thr Ser  Pro Ala Ala
                    995                 1000                1005

Pro Val  Ser Tyr Ala Asp Met  Arg Thr Gly Ile Ala  Ala Glu Glu
            1010                1015                1020

Val Ser  Leu Pro Arg Ala Thr  Met Ala Ala Ala Ser  Ser Ser Ser
            1025                1030                1035

Ala Ala  Ser Ala Ser Pro Thr  Gly Pro Gln Gly Ala  Ala Glu Leu
            1040                1045                1050

Ala Ala  His Ser Ser Leu Leu  Gly Gly Pro Gln Gly  Pro Gly Gly
            1055                1060                1065

Met Ser  Ala Phe Thr Arg Val  Asn Leu Ser Pro Asn  Arg Asn Gln
            1070                1075                1080

Ser Ala  Lys Val Ile Arg Ala  Asp Pro Gln Gly Cys  Arg Arg Arg
            1085                1090                1095

His Ser  Ser Glu Thr Phe Ser  Ser Thr Pro Ser Ala  Thr Arg Val
            1100                1105                1110

Gly Asn  Thr Val Pro Phe Gly  Ala Gly Ala Ala Val  Gly Gly Gly
            1115                1120                1125

Gly Gly  Ser Ser Ser Ser Ser  Glu Asp Val Lys Arg  His Ser Ser
            1130                1135                1140

Ala Ser  Phe Glu Asn Val Trp  Leu Arg Pro Gly Glu  Leu Gly Gly
            1145                1150                1155

Ala Pro  Lys Glu Pro Ala Lys  Leu Cys Gly Ala Ala  Gly Gly Leu
            1160                1165                1170

Glu Asn  Gly Leu Asn Tyr Ile  Asp Leu Asp Leu Val  Lys Asp Phe
            1175                1180                1185

Lys Gln  Cys Pro Gln Glu Cys  Thr Pro Glu Pro Gln  Pro Pro Pro
            1190                1195                1200

Pro Pro  Pro Pro His Gln Pro  Leu Gly Ser Gly Glu  Ser Ser Ser
            1205                1210                1215

Thr Arg  Arg Ser Ser Glu Asp  Leu Ser Ala Tyr Ala  Ser Ile Ser
            1220                1225                1230

Phe Gln  Lys Gln Pro Glu Asp  Arg Gln
            1235                1240

<210> SEQ ID NO 2
<211> LENGTH: 1324
<212> TYPE: PRT
<213> ORGANISM: Homo sapiens
```

```
<400> SEQUENCE: 2

Met Ala Ser Pro Pro Arg His Gly Pro Pro Gly Pro Ala Ser Gly Asp
  1               5                  10                  15

Gly Pro Asn Leu Asn Asn Asn Asn Asn Asn His Ser Val Arg
             20                  25                  30

Lys Cys Gly Tyr Leu Arg Lys Gln Lys His Gly His Lys Arg Phe Phe
             35                  40                  45

Val Leu Arg Gly Pro Gly Ala Gly Gly Asp Lys Ala Thr Ala Gly Gly
     50                  55                  60

Gly Ser Ala Pro Gln Pro Pro Arg Leu Glu Tyr Tyr Glu Ser Glu Lys
 65                  70                  75                  80

Asn Trp Arg Ser Lys Ala Gly Ala Pro Lys Arg Val Ile Ala Leu Asp
                 85                  90                  95

Cys Cys Leu Asn Ile Asn Lys Arg Ala Asp Pro Lys His Lys Tyr Leu
                100                 105                 110

Ile Ala Leu Tyr Thr Lys Asp Glu Tyr Phe Ala Val Ala Ala Glu Asn
                115                 120                 125

Glu Gln Glu Gln Glu Gly Trp Tyr Arg Ala Leu Thr Asp Leu Val Ser
    130                 135                 140

Glu Gly Arg Ala Ala Ala Gly Asp Ala Pro Ala Ala Ala Pro Ala
145                 150                 155                 160

Ala Ser Cys Ser Ala Ser Leu Pro Gly Ala Val Gly Gly Ser Ala Gly
                165                 170                 175

Ala Ala Gly Ala Glu Asp Ser Tyr Gly Leu Val Ala Pro Ala Thr Ala
                180                 185                 190

Ala Tyr Arg Glu Val Trp Gln Val Asn Leu Lys Pro Lys Gly Leu Gly
                195                 200                 205

Gln Ser Lys Asn Leu Thr Gly Val Tyr Arg Leu Cys Leu Ser Ala Arg
    210                 215                 220

Thr Ile Gly Phe Val Lys Leu Asn Cys Glu Gln Pro Ser Val Thr Leu
225                 230                 235                 240

Gln Leu Met Asn Ile Arg Arg Cys Gly His Ser Asp Ser Phe Phe Phe
                245                 250                 255

Ile Glu Val Gly Arg Ser Ala Val Thr Gly Pro Gly Glu Leu Trp Met
                260                 265                 270

Gln Ala Asp Asp Ser Val Val Ala Gln Asn Ile His Glu Thr Ile Leu
    275                 280                 285

Glu Ala Met Lys Ala Leu Lys Glu Leu Phe Glu Phe Arg Pro Arg Ser
    290                 295                 300

Lys Ser Gln Ser Ser Gly Ser Ser Ala Thr His Pro Ile Ser Val Pro
305                 310                 315                 320

Gly Ala Arg Arg His His His Leu Val Asn Leu Pro Pro Ser Gln Thr
                325                 330                 335

Gly Leu Val Arg Arg Ser Arg Thr Asp Ser Leu Ala Ala Thr Pro Pro
                340                 345                 350

Ala Ala Lys Cys Ser Ser Cys Arg Val Arg Thr Ala Ser Glu Gly Asp
                355                 360                 365

Gly Gly Ala Ala Ala Gly Ala Ala Ala Gly Ala Arg Pro Val Ser
    370                 375                 380

Val Ala Gly Ser Pro Leu Ser Pro Gly Pro Val Arg Ala Pro Leu Ser
385                 390                 395                 400

Arg Ser His Thr Leu Ile Gly Gly Cys Arg Ala Ala Gly Thr Lys Trp
```

-continued

```
                405                 410                 415
His Cys Phe Pro Ala Gly Gly Gly Leu Gln His Ser Arg Ser Met Ser
                420                 425                 430

Met Pro Val Glu His Leu Pro Pro Ala Ala Thr Ser Pro Gly Ser Leu
                435                 440                 445

Ser Ser Ser Ser Asp His Gly Trp Gly Ser Tyr Pro Pro Pro Pro Gly
                450                 455                 460

Pro His Pro Leu Leu Pro His Pro Leu His His Gly Pro Gly Gln Arg
465                 470                 475                 480

Pro Ser Ser Gly Ser Ala Ser Ala Ser Gly Ser Pro Ser Asp Pro Gly
                485                 490                 495

Phe Met Ser Leu Asp Glu Tyr Gly Ser Ser Pro Gly Asp Leu Arg Ala
                500                 505                 510

Phe Cys Ser His Arg Ser Asn Thr Pro Glu Ser Ile Ala Glu Thr Pro
                515                 520                 525

Pro Ala Arg Asp Gly Gly Gly Gly Glu Phe Tyr Gly Tyr Met Thr
                530                 535                 540

Met Asp Arg Pro Leu Ser His Cys Gly Arg Ser Tyr Arg Arg Val Ser
545                 550                 555                 560

Gly Asp Ala Ala Gln Asp Leu Asp Arg Gly Leu Arg Lys Arg Thr Tyr
                565                 570                 575

Ser Leu Thr Thr Pro Ala Arg Gln Arg Pro Val Pro Gln Pro Ser Ser
                580                 585                 590

Ala Ser Leu Asp Glu Tyr Thr Leu Met Arg Ala Thr Phe Ser Gly Ser
                595                 600                 605

Ala Gly Arg Leu Cys Pro Ser Cys Pro Ala Ser Ser Pro Lys Val Ala
                610                 615                 620

Tyr His Pro Tyr Pro Glu Asp Tyr Gly Asp Ile Glu Ile Gly Ser His
625                 630                 635                 640

Arg Ser Ser Ser Asn Leu Gly Ala Asp Asp Gly Tyr Met Pro Met
                645                 650                 655

Thr Pro Gly Ala Ala Leu Ala Gly Ser Gly Ser Gly Ser Cys Arg Ser
                660                 665                 670

Asp Asp Tyr Met Pro Met Ser Pro Ala Ser Val Ser Ala Pro Lys Gln
                675                 680                 685

Ile Leu Gln Pro Arg Ala Ala Ala Ala Ala Ala Ala Val Pro Phe
                690                 695                 700

Ala Gly Pro Ala Gly Pro Ala Pro Thr Phe Ala Ala Gly Arg Thr Phe
705                 710                 715                 720

Pro Ala Ser Gly Gly Gly Tyr Lys Ala Ser Ser Pro Ala Glu Ser Ser
                725                 730                 735

Pro Glu Asp Ser Gly Tyr Met Arg Met Trp Cys Gly Ser Lys Leu Ser
                740                 745                 750

Met Glu His Ala Asp Gly Lys Leu Leu Pro Asn Gly Asp Tyr Leu Asn
                755                 760                 765

Val Ser Pro Ser Asp Ala Val Thr Thr Gly Thr Pro Asp Phe Phe
                770                 775                 780

Ser Ala Ala Leu His Pro Gly Gly Glu Pro Leu Arg Gly Val Pro Gly
785                 790                 795                 800

Cys Cys Tyr Ser Ser Leu Pro Arg Ser Tyr Lys Ala Pro Tyr Thr Cys
                805                 810                 815

Gly Gly Asp Ser Asp Gln Tyr Val Leu Met Ser Ser Pro Val Gly Arg
                820                 825                 830
```

```
Ile Leu Glu Glu Glu Arg Leu Glu Pro Gln Ala Thr Pro Gly Pro Thr
        835                 840                 845

Gln Ala Ala Ser Ala Phe Gly Ala Gly Pro Thr Gln Pro Pro His Pro
    850                 855                 860

Val Val Pro Ser Pro Val Arg Pro Ser Gly Gly Arg Pro Glu Gly Phe
865                 870                 875                 880

Leu Gly Gln Arg Gly Arg Ala Val Arg Pro Thr Arg Leu Ser Leu Glu
                885                 890                 895

Gly Leu Pro Ser Leu Pro Ser Met His Glu Tyr Pro Leu Pro Pro Glu
                900                 905                 910

Pro Lys Ser Pro Gly Glu Tyr Ile Asn Ile Asp Phe Gly Glu Pro Gly
                915                 920                 925

Ala Arg Leu Ser Pro Pro Ala Pro Pro Leu Leu Ala Ser Ala Ala Ser
            930                 935                 940

Ser Ser Ser Leu Leu Ser Ala Ser Ser Pro Ala Leu Ser Leu Gly Ser
945                 950                 955                 960

Gly Thr Pro Gly Thr Ser Ser Asp Ser Arg Gln Arg Ser Pro Leu Ser
                965                 970                 975

Asp Tyr Met Asn Leu Asp Phe Ser Ser Pro Lys Ser Pro Lys Pro Gly
            980                 985                 990

Ala Pro Ser Gly His Pro Val Gly Ser Leu Asp Gly Leu Leu Ser Pro
            995                 1000                1005

Glu Ala Ser Ser Pro Tyr Pro Pro Leu Pro Pro Arg Pro Ser Ala
        1010                1015                1020

Ser Pro Ser Ser Ser Leu Gln Pro Pro Pro Pro Pro Ala Pro
        1025                1030                1035

Gly Glu Leu Tyr Arg Leu Pro Pro Ala Ser Ala Val Ala Thr Ala
        1040                1045                1050

Gln Gly Pro Gly Ala Ala Ser Ser Leu Ser Ser Asp Thr Gly Asp
        1055                1060                1065

Asn Gly Asp Tyr Thr Glu Met Ala Phe Gly Val Ala Ala Thr Pro
        1070                1075                1080

Pro Gln Pro Ile Ala Ala Pro Pro Lys Pro Glu Ala Ala Arg Val
        1085                1090                1095

Ala Ser Pro Thr Ser Gly Val Lys Arg Leu Ser Leu Met Glu Gln
        1100                1105                1110

Val Ser Gly Val Glu Ala Phe Leu Gln Ala Ser Gln Pro Pro Asp
        1115                1120                1125

Pro His Arg Gly Ala Lys Val Ile Arg Ala Asp Pro Gln Gly Gly
        1130                1135                1140

Arg Arg Arg His Ser Ser Glu Thr Phe Ser Ser Thr Thr Thr Val
        1145                1150                1155

Thr Pro Val Ser Pro Ser Phe Ala His Asn Pro Lys Arg His Asn
        1160                1165                1170

Ser Ala Ser Val Glu Asn Val Ser Leu Arg Lys Ser Ser Glu Gly
        1175                1180                1185

Gly Val Gly Val Gly Pro Gly Gly Gly Asp Glu Pro Pro Thr Ser
        1190                1195                1200

Pro Arg Gln Leu Gln Pro Ala Pro Pro Leu Ala Pro Gln Gly Arg
        1205                1210                1215

Pro Trp Thr Pro Gly Gln Pro Gly Gly Leu Val Gly Cys Pro Gly
        1220                1225                1230
```

```
Ser Gly Gly Ser Pro Met Arg Arg Glu Thr Ser Ala Gly Phe Gln
    1235                1240                1245

Asn Gly Leu Lys Tyr Ile Ala Ile Asp Val Arg Glu Glu Pro Gly
    1250                1255                1260

Leu Pro Pro Gln Pro Gln Pro Pro Pro Pro Leu Pro Gln Pro
    1265                1270                1275

Gly Asp Lys Ser Ser Trp Gly Arg Thr Arg Ser Leu Gly Gly Leu
    1280                1285                1290

Ile Ser Ala Val Gly Val Gly Ser Thr Arg Gly Cys Gly Gly
    1295                1300                1305

Pro Gly Pro Gly Ala Pro Ala Pro Cys Pro Thr Thr Tyr Ala Gln
    1310                1315                1320

His

<210> SEQ ID NO 3
<211> LENGTH: 1231
<212> TYPE: PRT
<213> ORGANISM: Mus musculus

<400> SEQUENCE: 3

Met Ala Ser Pro Pro Asp Thr Asp Gly Phe Ser Asp Val Arg Lys Val
1               5                   10                  15

Gly Tyr Leu Arg Lys Pro Lys Ser Met His Lys Arg Phe Phe Val Leu
                20                  25                  30

Arg Ala Ala Ser Glu Ala Gly Gly Pro Ala Arg Leu Glu Tyr Tyr Glu
            35                  40                  45

Asn Glu Lys Lys Trp Arg His Lys Ser Ser Ala Pro Lys Arg Ser Ile
        50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Ala His His Asp Gly Ala Gly Gly Gly Cys
        115                 120                 125

Gly Gly Ser Cys Ser Gly Ser Ser Gly Val Gly Glu Ala Gly Glu Asp
    130                 135                 140

Leu Ser Tyr Asp Thr Gly Pro Gly Pro Ala Phe Lys Glu Val Trp Gln
145                 150                 155                 160

Val Ile Leu Lys Pro Lys Gly Leu Gly Gln Thr Lys Asn Leu Ile Gly
                165                 170                 175

Ile Tyr Arg Leu Cys Leu Thr Ser Lys Thr Ile Ser Phe Val Lys Leu
            180                 185                 190

Asn Ser Glu Ala Ala Ala Val Val Leu Gln Leu Met Asn Ile Arg Arg
        195                 200                 205

Cys Gly His Ser Glu Asn Phe Phe Phe Ile Glu Val Gly Arg Ser Ala
    210                 215                 220

Val Thr Gly Pro Gly Glu Phe Trp Met Gln Val Asp Asp Ser Val Val
225                 230                 235                 240

Ala Gln Asn Met His Glu Thr Ile Leu Glu Ala Met Arg Ala Met Ser
                245                 250                 255

Asp Glu Phe Arg Pro Arg Ser Lys Ser Gln Ser Ser Ser Cys Ser
            260                 265                 270
```

```
Asn Pro Ile Ser Val Pro Leu Arg Arg His His Leu Asn Asn Pro Pro
    275                 280                 285

Pro Ser Gln Val Gly Leu Thr Arg Arg Ser Arg Thr Glu Ser Ile Thr
    290                 295                 300

Ala Thr Ser Pro Ala Ser Met Val Gly Lys Pro Gly Ser Phe Arg
305                 310                 315                 320

Val Arg Ala Ser Ser Asp Gly Glu Gly Thr Met Ser Arg Pro Ala Ser
                325                 330                 335

Val Asp Gly Ser Pro Val Ser Pro Ser Thr Asn Arg Thr His Ala His
            340                 345                 350

Arg His Arg Gly Ser Ser Arg Leu His Pro Pro Leu Asn His Ser Arg
                355                 360                 365

Ser Ile Pro Met Pro Ser Ser Arg Cys Ser Pro Ser Ala Thr Ser Pro
    370                 375                 380

Val Ser Leu Ser Ser Ser Ser Thr Ser Gly His Gly Ser Thr Ser Asp
385                 390                 395                 400

Cys Leu Phe Pro Arg Arg Ser Ser Ala Ser Val Ser Gly Ser Pro Ser
                405                 410                 415

Asp Gly Gly Phe Ile Ser Ser Asp Glu Tyr Gly Ser Ser Pro Cys Asp
            420                 425                 430

Phe Arg Ser Ser Phe Arg Ser Val Thr Pro Asp Ser Leu Gly His Thr
                435                 440                 445

Pro Pro Ala Arg Gly Glu Glu Glu Leu Ser Asn Tyr Ile Cys Met Gly
    450                 455                 460

Gly Lys Gly Ala Ser Thr Leu Ala Ala Pro Asn Gly His Tyr Ile Leu
465                 470                 475                 480

Ser Arg Gly Gly Asn Gly His Arg Tyr Ile Pro Gly Ala Asn Leu Gly
                485                 490                 495

Thr Ser Pro Ala Leu Pro Gly Asp Glu Ala Ala Gly Ala Ala Asp Leu
            500                 505                 510

Asp Asn Arg Phe Arg Lys Arg Thr His Ser Ala Gly Thr Ser Pro Thr
                515                 520                 525

Ile Ser His Gln Lys Thr Pro Ser Gln Ser Ser Val Ala Ser Ile Glu
    530                 535                 540

Glu Tyr Thr Glu Met Met Pro Ala Ala Tyr Pro Pro Gly Gly Gly Ser
545                 550                 555                 560

Gly Gly Arg Leu Pro Gly Tyr Arg His Ser Ala Phe Val Pro Thr His
                565                 570                 575

Ser Tyr Pro Glu Glu Gly Leu Glu Met His His Leu Glu Arg Arg Gly
            580                 585                 590

Gly His His Arg Pro Asp Thr Ser Asn Leu His Thr Asp Asp Gly Tyr
                595                 600                 605

Met Pro Met Ser Pro Gly Val Ala Pro Val Pro Ser Asn Arg Lys Gly
    610                 615                 620

Asn Gly Asp Tyr Met Pro Met Ser Pro Lys Ser Val Ser Ala Pro Gln
625                 630                 635                 640

Gln Ile Ile Asn Pro Ile Arg Arg His Pro Gln Arg Val Asp Pro Asn
                645                 650                 655

Gly Tyr Met Met Met Ser Pro Ser Gly Ser Cys Ser Pro Asp Ile Gly
            660                 665                 670

Gly Gly Ser Ser Ser Ser Ser Ile Ser Ala Ala Pro Ser Gly Ser
                675                 680                 685

Ser Tyr Gly Lys Pro Trp Thr Asn Gly Val Gly Gly His His Thr His
```

-continued

```
            690                 695                 700
Ala Leu Pro His Ala Lys Pro Val Glu Ser Gly Gly Gly Lys Leu
705                 710                 715                 720

Leu Pro Cys Thr Gly Asp Tyr Met Asn Met Ser Pro Val Gly Asp Ser
                    725                 730                 735

Asn Thr Ser Ser Pro Ser Glu Cys Tyr Tyr Gly Pro Glu Asp Pro Gln
                740                 745                 750

His Lys Pro Val Leu Ser Tyr Tyr Ser Leu Pro Arg Ser Phe Lys His
            755                 760                 765

Thr Gln Arg Pro Gly Glu Pro Glu Gly Ala Arg His Gln His Leu
770                 775                 780

Arg Leu Ser Ser Ser Gly Arg Leu Arg Tyr Thr Ala Thr Ala Glu
785                 790                 795                 800

Asp Ser Ser Ser Thr Ser Ser Asp Ser Leu Gly Gly Gly Tyr Cys
                    805                 810                 815

Gly Ala Arg Pro Glu Ser Ser Leu Thr His Pro His His Val Leu
                820                 825                 830

Gln Pro His Leu Pro Arg Lys Val Asp Thr Ala Ala Gln Thr Asn Ser
                835                 840                 845

Arg Leu Ala Arg Pro Thr Arg Leu Ser Leu Gly Asp Pro Lys Ala Ser
850                 855                 860

Thr Leu Pro Arg Val Arg Glu Gln Gln Gln Gln Gln Ser Ser Leu
865                 870                 875                 880

His Pro Pro Glu Pro Lys Ser Pro Gly Glu Tyr Val Asn Ile Glu Phe
                    885                 890                 895

Gly Ser Gly Gln Pro Gly Tyr Leu Ala Gly Pro Ala Thr Ser Arg Ser
                900                 905                 910

Ser Pro Ser Val Arg Cys Pro Pro Gln Leu His Pro Ala Pro Arg Glu
            915                 920                 925

Glu Thr Gly Ser Glu Glu Tyr Met Asn Met Asp Leu Gly Pro Gly Arg
930                 935                 940

Arg Ala Thr Trp Gln Glu Ser Gly Gly Val Glu Leu Gly Arg Ile Gly
945                 950                 955                 960

Pro Ala Pro Pro Gly Ser Ala Thr Val Cys Arg Pro Thr Arg Ser Val
                    965                 970                 975

Pro Asn Ser Arg Gly Asp Tyr Met Thr Met Gln Ile Gly Cys Pro Arg
                980                 985                 990

Gln Ser Tyr Val Asp Thr Ser Pro Val Ala Pro Val Ser Tyr Ala Asp
            995                 1000                1005

Met Arg Thr Gly Ile Ala Ala Glu Lys Ala Ser Leu Pro Arg Pro
1010                1015                1020

Thr Gly Ala Ala Pro Pro Ser Ser Thr Ala Ser Ser Ser Val
1025                1030                1035

Thr Pro Gln Gly Ala Thr Ala Glu Gln Ala Thr His Ser Ser Leu
    1040                1045                1050

Leu Gly Gly Pro Gln Gly Pro Gly Gly Met Ser Ala Phe Thr Arg
    1055                1060                1065

Val Asn Leu Ser Pro Asn His Asn Gln Ser Ala Lys Val Ile Arg
    1070                1075                1080

Ala Asp Thr Gln Gly Cys Arg Arg Arg His Ser Ser Glu Thr Phe
    1085                1090                1095

Ser Ala Pro Thr Arg Ala Gly Asn Thr Val Pro Phe Gly Ala Gly
    1100                1105                1110
```

```
Ala Ala Val Gly Gly Ser Gly Gly Gly Gly Gly Ser Glu
    1115                1120                1125

Asp Val Lys Arg His Ser Ala Ser Phe Glu Asn Val Trp Leu
    1130                1135            1140

Arg Pro Gly Asp Leu Gly Gly Val Ser Lys Glu Ser Ala Pro Val
    1145                1150                1155

Cys Gly Ala Ala Gly Gly Leu Glu Lys Ser Leu Asn Tyr Ile Asp
    1160                1165                1170

Leu Asp Leu Ala Lys Glu Arg Ser Gln Asp Cys Pro Ser Gln Gln
    1175                1180                1185

Gln Ser Leu Pro Pro Pro Pro His Gln Pro Leu Gly Ser Asn
    1190                1195                1200

Glu Gly Asn Ser Pro Arg Arg Ser Ser Glu Asp Leu Ser Asn Tyr
    1205                1210                1215

Ala Ser Ile Ser Phe Gln Lys Gln Pro Glu Asp Arg Gln
    1220                1225                1230

<210> SEQ ID NO 4
<211> LENGTH: 1321
<212> TYPE: PRT
<213> ORGANISM: Mus musculus

<400> SEQUENCE: 4

Met Ala Ser Ala Pro Leu Pro Gly Pro Pro Ala Ser Gly Gly Asp
1               5                   10                  15

Gly Pro Asn Leu Asn Asn Asn Asn Asn Asn Asn His Ser Val Arg
                20                  25                  30

Lys Cys Gly Tyr Leu Arg Lys Gln Lys His Gly His Lys Arg Phe Phe
                35                  40                  45

Val Leu Arg Gly Pro Gly Thr Gly Gly Asp Glu Ala Ser Ala Ala Gly
    50                  55                  60

Gly Ser Pro Pro Gln Pro Pro Arg Leu Glu Tyr Tyr Glu Ser Glu Lys
65                  70                  75                  80

Lys Trp Arg Ser Lys Ala Gly Ala Pro Lys Arg Val Ile Ala Leu Asp
                85                  90                  95

Cys Cys Leu Asn Ile Asn Lys Arg Ala Asp Ala Lys His Lys Tyr Leu
                100                 105                 110

Ile Ala Leu Tyr Thr Lys Asp Glu Tyr Phe Ala Val Ala Ala Glu Asn
                115                 120                 125

Glu Gln Glu Gln Glu Gly Trp Tyr Arg Ala Leu Thr Asp Leu Val Ser
    130                 135                 140

Glu Gly Arg Ser Gly Glu Gly Gly Ser Gly Thr Thr Gly Gly Ser Cys
145                 150                 155                 160

Ser Ala Ser Leu Pro Gly Val Leu Gly Gly Ser Ala Gly Ala Ala Gly
                165                 170                 175

Cys Asp Asp Asn Tyr Gly Leu Val Thr Pro Thr Ala Val Tyr Arg
                180                 185                 190

Glu Val Trp Gln Val Asn Leu Lys Pro Lys Gly Leu Gly Gln Ser Lys
                195                 200                 205

Asn Leu Thr Gly Val Tyr Arg Leu Cys Leu Ser Ala Arg Thr Ile Gly
    210                 215                 220

Phe Val Lys Leu Asn Cys Glu Gly Pro Ser Val Thr Leu Gln Leu Asn
225                 230                 235                 240

Asn Ile Arg Arg Cys Gly His Ser Asp Ser Phe Phe Phe Ile Glu Val
```

-continued

```
            245                 250                 255
Gly Arg Ser Ala Val Thr Gly Pro Gly Glu Leu Trp Met Gln Ala Asp
                260                 265                 270

Asp Ser Val Val Ala Gln Asn Ile His Glu Thr Ile Leu Glu Ala Met
            275                 280                 285

Lys Ala Leu Lys Glu Leu Phe Glu Phe Arg Pro Arg Ser Lys Ser Gln
        290                 295                 300

Ser Ser Gly Ser Ser Ala Thr His Pro Ile Ser Val Pro Gly Ala Arg
305                 310                 315                 320

Arg His His His Leu Val Asn Leu Pro Pro Ser Gln Thr Gly Leu Val
                325                 330                 335

Arg Arg Ser Arg Thr Asp Ser Leu Ala Ala Thr Pro Pro Ala Ala Lys
            340                 345                 350

Cys Thr Ser Cys Arg Val Arg Thr Ala Ser Glu Gly Asp Gly Gly Ala
        355                 360                 365

Ala Gly Gly Ala Gly Thr Ala Gly Gly Arg Pro Met Ser Val Ala Gly
        370                 375                 380

Ser Pro Leu Ser Pro Gly Pro Val Arg Ala Pro Leu Ser Arg Ser His
385                 390                 395                 400

Thr Leu Ser Ala Gly Cys Gly Gly Arg Pro Ser Lys Val Thr Leu Ala
                405                 410                 415

Pro Ala Gly Gly Ala Leu Gln His Ser Arg Ser Asn Ser Met Pro Val
            420                 425                 430

Ala His Ser Pro Pro Ala Ala Thr Ser Pro Gly Ser Leu Ser Ser Ser
        435                 440                 445

Ser Gly His Gly Ser Gly Ser Tyr Pro Leu Pro Pro Gly Ser His Pro
        450                 455                 460

His Leu Pro His Pro Leu His His Pro Gln Gly Gln Arg Pro Ser Ser
465                 470                 475                 480

Gly Ser Ala Ser Ala Ser Gly Ser Pro Ser Asp Pro Gly Phe Met Ser
                485                 490                 495

Leu Asp Glu Tyr Gly Ser Ser Pro Gly Asp Leu Arg Ala Phe Ser Ser
            500                 505                 510

His Arg Ser Asn Thr Pro Glu Ser Ile Ala Glu Thr Pro Pro Ala Arg
        515                 520                 525

Asp Gly Ser Gly Gly Glu Leu Tyr Gly Tyr Met Ser Met Asp Arg Pro
        530                 535                 540

Leu Ser His Cys Gly Arg Pro Tyr Arg Arg Val Ser Gly Asp Gly Ala
545                 550                 555                 560

Gln Asp Leu Asp Arg Gly Leu Arg Lys Arg Thr Tyr Ser Leu Thr Thr
                565                 570                 575

Pro Ala Arg Gln Arg Gln Val Pro Gln Pro Ser Ser Ala Ser Leu Asp
            580                 585                 590

Glu Tyr Thr Leu Met Arg Ala Thr Phe Ser Gly Ser Ser Gly Arg Leu
        595                 600                 605

Cys Pro Ser Phe Pro Ala Ser Ser Pro Lys Val Ala Tyr Asn Pro Tyr
        610                 615                 620

Pro Glu Asp Tyr Gly Asp Ile Glu Ile Gly Ser His Lys Ser Ser Ser
625                 630                 635                 640

Ser Asn Leu Gly Ala Asp Asp Gly Tyr Met Pro Met Thr Pro Gly Ala
                645                 650                 655

Ala Leu Arg Ser Gly Gly Pro Asn Ser Cys Lys Ser Asp Asp Tyr Met
            660                 665                 670
```

```
Pro Met Ser Pro Thr Ser Val Ser Ala Pro Lys Gln Ile Leu Gln Pro
        675                 680                 685

Arg Leu Ala Ala Ala Leu Pro Pro Ser Gly Ala Ala Val Pro Ala Pro
    690                 695                 700

Pro Ser Gly Val Gly Arg Thr Phe Pro Val Asn Gly Gly Gly Tyr Lys
705                 710                 715                 720

Ala Ser Ser Pro Ala Glu Ser Ser Pro Glu Asp Ser Gly Tyr Met Arg
                725                 730                 735

Met Trp Cys Gly Ser Lys Leu Ser Met Glu Asn Pro Asp Pro Lys Leu
            740                 745                 750

Leu Pro Asn Gly Asp Tyr Leu Asn Lys Ser Pro Ser Glu Ala Gly Thr
        755                 760                 765

Ala Gly Thr Pro Pro Asp Phe Ser Ala Ala Leu Arg Gly Gly Ser Glu
    770                 775                 780

Gly Leu Lys Gly Ile Pro Gly His Cys Tyr Ser Ser Leu Pro Arg Ser
785                 790                 795                 800

Tyr Lys Ala Pro Cys Ser Cys Ser Gly Asp Asn Asp Gln Tyr Val Leu
                805                 810                 815

Met Ser Ser Pro Val Gly Arg Ile Leu Glu Glu Arg Leu Glu Pro
            820                 825                 830

Gln Ala Thr Pro Gly Ala Gly Thr Phe Gly Ala Ala Gly Gly Ser His
        835                 840                 845

Thr Gln Pro His His Ser Ala Val Pro Ser Ser Met Arg Pro Ser Ala
    850                 855                 860

Ile Gly Gly Arg Pro Glu Gly Phe Leu Gly Gln Arg Cys Arg Ala Val
865                 870                 875                 880

Arg Pro Thr Arg Leu Ser Leu Glu Gly Leu Gln Thr Leu Pro Ser Met
                885                 890                 895

Gln Glu Tyr Pro Leu Pro Thr Glu Pro Lys Ser Pro Gly Glu Tyr Ile
            900                 905                 910

Asn Ile Asp Pro Gly Glu Ala Gly Thr Arg Leu Ser Pro Ala Pro
        915                 920                 925

Pro Leu Leu Ala Ser Ala Ala Ser Ser Ser Leu Leu Ser Ala Ser
    930                 935                 940

Ser Pro Ala Ser Ser Leu Gly Ser Gly Thr Pro Gly Thr Ser Ser Asp
945                 950                 955                 960

Ser Arg Gln Arg Ser Pro Leu Ser Asp Tyr Met Asn Leu Asp Pro Ser
                965                 970                 975

Ser Pro Lys Ser Pro Lys Pro Ser Thr Arg Ser Gly Asp Thr Val Gly
            980                 985                 990

Ser Met Asp Gly Leu Leu Ser Pro Glu Ala Ser Ser Pro Tyr Pro Pro
        995                 1000                1005

Leu Pro Pro Arg Pro Ser Thr Ser Pro Ser Ser Leu Gln Gln Pro
    1010                1015                1020

Leu Pro Pro Ala Pro Gly Asp Leu Tyr Arg Leu Pro Pro Ala Ser
    1025                1030                1035

Ala Ala Thr Ser Gln Gly Pro Thr Ala Gly Ser Ser Met Ser Ser
    1040                1045                1050

Glu Pro Gly Asp Asn Gly Asp Tyr Ser Glu Met Ala Phe Gly Val
    1055                1060                1065

Ala Ala Thr Pro Pro Gln Pro Ile Val Ala Pro Pro Lys Pro Glu
    1070                1075                1080
```

```
Gly Ala Arg Val Ala Ser Pro Thr Ser Gly Leu Lys Arg Leu Ser
    1085                1090                1095

Leu Met Asp Gln Val Ser Gly Val Glu Ala Phe Leu Gln Val Ser
    1100                1105                1110

Gln Pro Pro Asp Pro His Arg Gly Ala Lys Val Ile Arg Ala Asp
    1115                1120                1125

Pro Gln Gly Gly Arg Arg His Ser Ser Glu Thr Phe Ser Ser
    1130                1135                1140

Thr Thr Thr Val Thr Pro Val Ser Pro Ser Phe Ala His Asn Ser
    1145                1150                1155

Lys Arg His Asn Ser Ala Ser Val Glu Asn Val Ser Leu Arg Lys
    1160                1165                1170

Ser Ser Glu Gly Ser Ser Thr Leu Gly Gly Gly Asp Glu Pro Pro
    1175                1180                1185

Thr Ser Pro Gly Gln Ala Gln Pro Leu Val Ala Val Pro Pro Val
    1190                1195                1200

Pro Gln Ala Arg Pro Trp Asn Pro Gly Gln Pro Gly Ala Leu Ile
    1205                1210                1215

Gly Cys Pro Gly Gly Ser Ser Ser Pro Met Arg Arg Glu Thr Ser
    1220                1225                1230

Val Gly Phe Gln Asn Gly Leu Asn Tyr Ile Ala Ile Asp Val Arg
    1235                1240                1245

Gly Glu Gln Gly Ser Leu Ala Gln Ser Gln Pro Gln Pro Gly Asp
    1250                1255                1260

Lys Asn Ser Trp Ser Arg Thr Arg Ser Leu Gly Gly Leu Leu Gly
    1265                1270                1275

Thr Val Gly Gly Ser Gly Ala Ser Gly Val Cys Gly Gly Pro Gly
    1280                1285                1290

Thr Gly Ala Leu Pro Ser Ala Ser Thr Tyr Ala Ser Ile Asp Phe
    1295                1300                1305

Leu Ser His His Leu Lys Glu Ala Thr Val Val Lys Glu
    1310                1315                1320

<210> SEQ ID NO 5
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; serine at position 8 is
      phosphorylated

<400> SEQUENCE: 5

Thr Arg Arg Ser Arg Thr Glu Ser Ile Thr Ala Thr Ser Pro Ala
1               5                   10                  15

<210> SEQ ID NO 6
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; serine at position 8 is
      phosphorylated

<400> SEQUENCE: 6

Ser Phe Arg Val Arg Ala Ser Ser Asp Gly Glu Gly Thr Met Ser
1               5                   10                  15
```

<210> SEQ ID NO 7
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; serine at position 8 is
      phosphorylated

<400> SEQUENCE: 7

Gly Cys Arg Arg Arg His Ser Ser Glu Thr Phe Ser Ser Thr Pro
1               5                   10                  15

<210> SEQ ID NO 8
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION; serine at position 8 is
      phosphorylated

<400> SEQUENCE: 8

Gly Gly Arg Arg Arg His Ser Ser Glu Thr Phe Ser Ser Thr Thr
1               5                   10                  15

<210> SEQ ID NO 9
<211> LENGTH: 15
<212> TYPE: PRT
<213> ORGANISM: Mus musculus
<220> FEATURE:
<221> NAME/KEY: MOD_RES
<222> LOCATION: (8)..(8)
<223> OTHER INFORMATION: PHOSPHORYLATION; serine at position 8 is
      phosphorylated

<400> SEQUENCE: 9

Gly Cys Arg Arg Arg His Ser Ser Glu Thr Phe Ser Ala Pro Thr
1               5                   10                  15

<210> SEQ ID NO 10
<211> LENGTH: 15
<212> TYPE: PRT
<213> ORGANISM: Mus musculus
<220> FEATURE:
<221> NAME/KEY: MOD_RES
<222> LOCATION: (8)..(8)
<223> OTHER INFORMATION: PHOSPHORYLATION; serine at position 8 is
      phosphorylated

<400> SEQUENCE: 10

Gly Gly Arg Arg Arg His Ser Ser Glu Thr Phe Ser Ser Thr Thr
1               5                   10                  15

<210> SEQ ID NO 11
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: PHOSPHORYLATION; serine at position 7 is
      phosphorylated -continued

```
<400> SEQUENCE: 11

Cys Arg Arg Arg His Ser Ser Glu Thr Phe Ser Ser Thr
1               5                   10
```